(12) United States Patent
Smith et al.

(10) Patent No.: US 12,102,615 B2
(45) Date of Patent: Oct. 1, 2024

(54) **SYNTHESIS OF NOVEL XYLOSE FREE OCCIDIOFUNGIN ANAL

(51) Int. Cl.
  *A61P 43/00*  (2006.01)
  *C07K 7/56*   (2006.01)
  *C07K 7/60*   (2006.01)
  *C07K 7/64*   (2006.01)

(56) References Cited

U.S. PATENT DOCUMENTS

2014/0147416 A1* 5/2014 Smith .................. C07K 7/56
                                              435/68.1
2016/0008423 A1  1/2016 Lu et al.
2017/0281721 A1 10/2017 Smith et al.

OTHER PUBLICATIONS

Lu et al., "Occidiofungin, a Unique Antifungal Glycopeptide Produced by a strain of Burkholderia contaminans" Biochemistry vol. 48 No. 35 pp. 8312-8321, doi: 10.1021/bi900814c. (Year: 2009).*
Written Opinion in International Application No. PCT/US2019/025989, Jun. 13, 2019, pp. 1-7.

* cited by examiner

Occidiofungin A: $R_1$ = H, $R_2$ = H, $R_3$ = H or (CO)CH$_2$CH$_2$CH$_2$C≡CH

Occidiofungin B: $R_1$ = OH, $R_2$ = H, $R_3$ = H or (CO)CH$_2$CH$_2$CH$_2$C≡CH

Occidiofungin C: $R_1$ = H, $R_2$ = Cl, $R_3$ = H or (CO)CH$_2$CH$_2$CH$_2$C≡CH

Occidiofungin D: $R_1$ = OH, $R_2$ = Cl, $R_3$ = H or (CO)CH$_2$CH$_2$CH$_2$C≡CH Occidiofungin A: $R_1$ = H, $R_2$ = H, $R_3$ = H or $(CO)CH_2CH_2CH_2C≡CH$ Occidiofungin B: $R_1$ = OH, $R_2$ = H, $R_3$ = H or $(CO)CH_2CH_2CH_2C≡CH$ Occidiofungin C: $R_1$ = H, $R_2$ = Cl, $R_3$ = H or $(CO)CH_2CH_2CH_2C≡CH$ Occidiofungin D: $R_1$ = OH, $R_2$ = Cl, $R_3$ = H or $(CO)CH_2CH_2CH_2C≡CH$ Occidiofungin A: $R_1$ = H, $R_2$ = H, $R_3$ = H or $(CO)CH_2CH_2CH_2C≡CH$ Occidiofungin B: $R_1$ = OH, $R_2$ = H, $R_3$ = H or $(CO)CH_2CH_2CH_2C≡CH$ Occidiofungin C: $R_1$ = H, $R_2$ = Cl, $R_3$ = H or $(CO)CH_2CH_2CH_2C≡CH$ Occidiofungin D: $R_1$ = OH, $R_2$ = Cl, $R_3$ = H or $(CO)CH_2CH_2CH_2C≡CH$ Occidiofungin A: $R_1$ = H, $R_2$ = H, $R_3$ = H or $(CO)CH_2CH_2CH_2C\equiv CH$ Occidiofungin B: $R_1$ = OH, $R_2$ = H, $R_3$ = H or $(CO)CH_2CH_2CH_2C\equiv CH$ Occidiofungin C: $R_1$ = H, $R_2$ = Cl, $R_3$ = H or $(CO)CH_2CH_2CH_2C\equiv CH$ Occidiofungin D: $R_1$ = OH, $R_2$ = Cl, $R_3$ = H or $(CO)CH_2CH_2CH_2C\equiv CH$ Occidiofungin A: $R_1$ = H, $R_2$ = H, $R_3$ = H or $(CO)CH_2CH_2CH_2C\equiv CH$ Occidiofungin B: $R_1$ = OH, $R_2$ = H, $R_3$ = H or $(CO)CH_2CH_2CH_2C\equiv CH$ Occidiofungin C: $R_1$ = H, $R_2$ = Cl, $R_3$ = H or $(CO)CH_2CH_2CH_2C\equiv CH$ Occidiofungin D: $R_1$ = OH, $R_2$ = Cl, $R_3$ = H or $(CO)CH_2CH_2CH_2C\equiv CH$

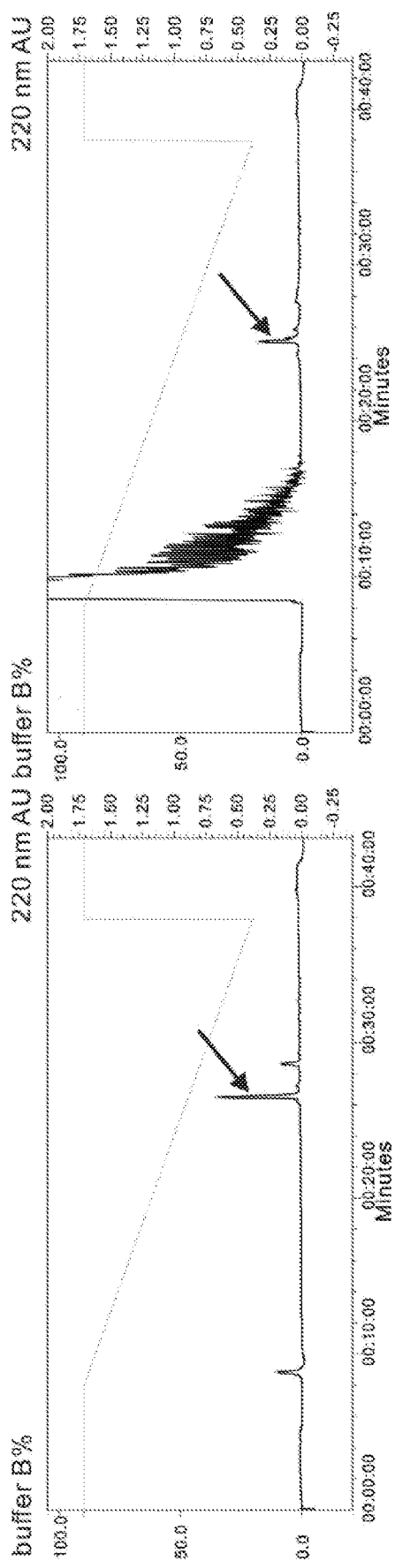
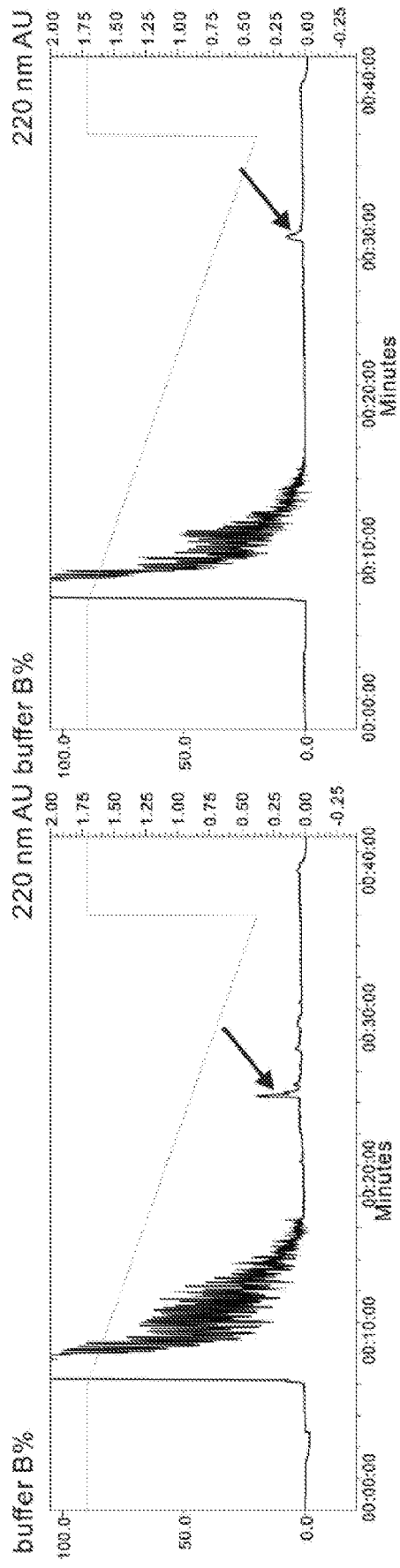
Figure 5A
Figure 5B
Figure 5C
Figure 5D

SYNTHESIS OF NOVEL XYLOSE FREE OCCIDIOFUNGIN ANALOGUES AND METHODS OF USING THEM

CROSS-REFERENCE TO RELATED APPLICATIONS

This application is the U.S. National Stage Application of International Patent Application No. PCT/US2019/025989, filed on Apr. 5, 2019, which claims the benefit of U.S. Provisional Application Ser. No. 62/653,253, filed Apr. 5, 2018, the disclosures of which are hereby incorporated by reference herein in their entirety, including all figures, tables and amino acid or nucleic sequences.

This invention was made with government support under 1R41A1122441-01A1 awarded by the NIH-NIAID. The government has certain rights in the invention.

The Sequence Listing for this application is labeled "Seq-List.txt" which was created on Apr. 5, 2019 and is 1 KB. The entire content of the sequence listing is incorporated herein by reference in its entirety.

BACKGROUND OF THE INVENTION

Fungal infections caused by pathogens that are resistant to commonly used classes of antifungals are becoming increasingly prevalent. A CDC report described the spread of multi-drug resistant *Candida auris* causing systemic infections in hospitalized patients. Furthermore, other species such as *Candida glabrata* and *Candida parapsilosis* have been reported to have gained resistance to routinely used azoles and echinocandins. An example of a fungal infection that is rapidly developing resistance to currently available treatments is vulvovaginal candidiasis (VVC). VVC affects approximately 75% of women and 5-10% of women develop recurrent VVC (RVVC). Approximately 90% of VVC is caused by *C. albicans*, while the remaining 10% is caused by *C. glabrata, Candida tropicalis, Candida parapsilosis* and *Candida krusei*. These non-*albicans* VVC causing species are generally resistant to azole treatments, which are the most common treatment option for VVC. No new therapeutic developments occurred in decades for RVVC. There is no established treatment method for VVC, which has led to the development of several ineffective treatment methods. These generally include the use of a rigorous dosing regimen of antifungals followed by a long period of prophylactic dosing.

*Candida* species are an important cause of infection and mortality in all hospitalized patients. Candidemia has a mortality rate of 30%-50% in cancer patients and is a major complicating factor in the treatment of cancer. Despite current antifungal drugs, invasive fungal infections are still a major cause of morbidity and mortality in transplant patients. Reports suggest that candidal infection is the first and second most common infection in lung and heart transplant recipients, respectively. In heart transplant recipients, candidal disease has been attributed to a mortality rate of 28%. A rise in candidemia caused by non-*albicans Candida* spp. and an increase in azole resistance is alarming; and supports the need for new antifungals. More appropriate antifungal treatment options may reduce the cost of treatment and mortality of patients.

Antifungals currently in clinical use primarily comprise of the polyenes, echinocandins and azoles. The polyene antifungal amphotericin B was introduced in the 1950s and was the only antifungal available until the introduction of the azole class of antifungals in the 1980s. These two groups primarily target ergosterol production or bind to ergosterol, disrupting the fungal membrane. The echinocandins, the third group, are synthetically modified lipopeptides that originate from a natural cyclic peptide produced by fungi. This group selectively inhibits 1,3-β-glucan synthesis by functioning as a non-competitive inhibitor of 1,3-β-glucan synthase. Widespread resistance and the ineffective spectrum of activity of these antifungals have been reported. The prevalence of echinocandin and azole-resistant fungal pathogens and the limited spectrum of activity of those compounds is one major issue contributing to the need for a new class of antifungals. Additionally, current antifungal treatments lead to abnormal liver and kidney function tests and have limitations with respect to their spectrum of activity and toxicities. Presumably, the identification of a novel class of antifungals with a broad spectrum of activity and a unique mechanism of action would mitigate the loss of life associated with the use of the current classes of antifungals. These limitations and toxicity problems have created an urgent need to identify antifungal compounds that have new fungal cell targets.

Occidiofungins, isolated from *Burkholderia contaminans* MS14, are a newly discovered class of antifungals. Occidiofungin is a non-ribosomally synthesized glycolipopeptide produced by *B. contaminans* MS14, a soil bacterium. It is a cyclic peptide with a base mass of 1200 Da (FIG. 1). The bacterium produces a mixture of structural analogues of the base compound (Occidiofungins A-D). However, all analogues are composed of eight amino acids and a C18 fatty amino acid (hereinafter, NAA) containing a xylose sugar, and a 2,4-diaminobutyric acid (DABA). The structural analogues differ by the addition of oxygen to asparagine 1 (Asn1) forming a β-hydroxy asparagine 1 (BHN1) and by the addition of chlorine to β-hydroxy tyrosine 4 (BHY) forming 3-chloro β-hydroxy tyrosine 4 (chloro-BHY). Occidiofungins (A-D) show promise for the development of novel therapeutics for treating fungal infections.

Improvements in the production of the occidiofungin B analog have been made. The method devised does not lead to a complex mixture of occidiofungin.

Mammalian glycoproteins containing xylose are not reported. Xylose is one of the main cross-reactive carbohydrate determinants (CCDs) that lead to an allergic response. An allergic or stress response was observed in mice following an intravenous administration of occidiofungin (A-D). Therefore, producing xylose free occidiofungin (OF-Δxyl) analogues and determining their efficacy against fungal infections is desirable.

BRIEF SUMMARY OF THE INVENTION

The invention provides methods for producing novel occidiofungin analogues that lack xylose (OF-Δxyl analogues) and methods of using OF-Δxyl analogues. In certain embodiments, OF-Δxyl analogues are aldehyde containing analogues. In certain embodiments, the aldehyde containing OF-Δxyl analogues are further modified to produce amine containing OF-Δxyl analogues, triazole containing OF-Δxyl analogues or hydrazones containing OF-Δxyl analogues. The aldehyde, amine, triazole or hydrazone containing OF-Δxyl analogues can be further modified to produce additional OF-Δxyl analogues. Various OF-Δxyl analogues described herein induce reduced inflammation and toxicity and have superior pharmacological properties compared to the natural occidiofungins. Accordingly, certain embodiments of the invention provide methods of controlling fungal infections by administering to the subjects in need thereof the OF-Δxyl analogues described herein.

BRIEF DESCRIPTION OF THE DRAWINGS

FIGS. 5A-5D. HPLC chromatograph of 100 μg of wild-type occidiofungin (A), aldehyde containing OF-Δxyl analogues following the reaction with undecylamine (B), dodecylamine (C), and DL-dihydrosphingosine D). The peak indicated by arrow is a desired product. Grey lines represent the gradient of buffer B (water with 0.1% TFA), while black lines represent the absorbance unit (AU) at 220 nm.

BRIEF DESCRIPTION OF THE SEQUENCES

Figure 1:
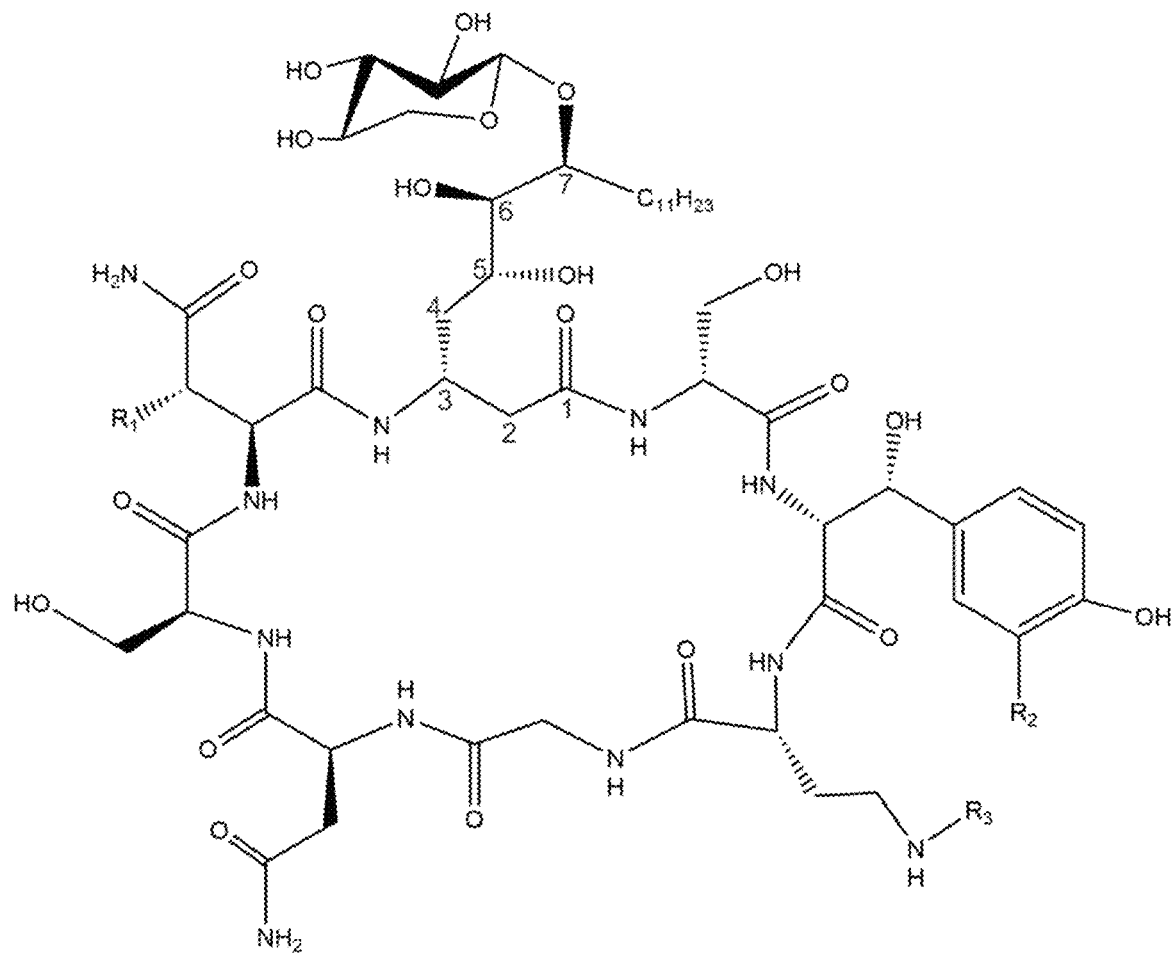
FIG. 1. Structure of occidiofungin. The location of the diol is at carbons 5 and 6 (as numbered in the Figure).

SEQ ID NO: 1: Sequence of cyclic occidiofungin antibiotic. Asn1-[Novel Amino Acid 2 (NAA2)-Ser3-BHY4-Gly6-Asn7-Ser8].

DETAILED DISCLOSURE OF THE INVENTION

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

When ranges are used herein, such as for dose ranges, combinations and subcombinations of ranges (e.g., subranges within the disclosed range), specific embodiments therein are intended to be explicitly included.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of an occidiofungin analogue of the invention that is pharmaceutically acceptable and that possesses the desired pharmacological activity of the parent occidiofungin analogue. In particular, such salts are non-toxic may be inorganic or organic acid addition salts and base addition salts.

"Pharmaceutically acceptable vehicle" refers to a diluent, adjuvant, excipient or carrier with which an occidiofungin analogue of the invention is administered. A "pharmaceutically acceptable vehicle" refers to a substance that is non-toxic, biologically tolerable, and otherwise biologically suitable for administration to a subject, such as an inert substance, added to a pharmacological composition or otherwise used to facilitate administration of an agent and that is compatible therewith. Examples of vehicles include but are not limited to calcium carbonate, calcium phosphate, various sugars and types of starch, cellulose derivatives, gelatin, vegetable oils, and polyethylene glycols.

"Subject" includes humans or non-human animals, particularly, mammals, such as bovine, porcine, canine, rodent, or feline animals.

"Treating" or "treatment" of any infection refers, in one embodiment, to ameliorating the infection (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the infection, either physically, (e.g., stabilization of a discernible symptom), physiologically, (e.g., stabilization of a physical parameter), or both. In yet another embodiment, "treating" or "treatment" refers to delaying the onset of the infection.

As used herein, the terms "reducing", "inhibiting", "blocking", "preventing", "alleviating", or "relieving" when referring to an occidiofungin analogue, mean that the occidiofungin analogue brings down the occurrence, severity, size, volume or associated symptoms of an infection by at least about 7.5%, 10%, 12.5%, 15%, 17.5%, 20%, 22.5%, 25%, 27.5%, 30%, 35%, 40%, 45%, 50%, 55%, 60%, 65%, 70%, 75%, 80%, 90%, or 100% compared to how the infection would normally exist without application of the OF-Δxyl analogue or a composition comprising the OF-Δxyl analogue.

In treatment methods according to the invention, a therapeutically effective amount of an OF-Δxyl analogues according to the invention is administered to a subject suffering from or diagnosed as having such an infection. A "therapeutically effective amount" means an amount or dose sufficient to generally bring about the desired therapeutic or prophylactic benefit in patients in need of such treatment for the designated infection.

Effective amounts or doses of the OF-Δxyl analogues of the present invention may be ascertained by routine methods such as modeling, dose escalation studies or clinical trials, and by taking into consideration routine factors, e.g., the mode or route of administration or drug delivery, the pharmacokinetics of the occidiofungin analogue, the severity and course of the infection, the subject's previous or ongoing therapy, the subject's health status and response to drugs, and the judgment of the treating physician. An example of a dose is in the range of from about 0.001 to about 200 mg of an occidiofungin analogue per kg of subject's body weight per day, preferably about 0.05 to 100 mg/kg/day, or about 1 to 35 mg/kg/day, even more preferably, about 1, 5, 10, or 20 mg/kg/day, in single or divided dosage units (e.g., BID, TID, QID). For a 70-kg human, an illustrative range for a suitable dosage amount is from about 0.05 to about 7 g/day, preferably, about 0.07 to about 2.45 g/day, even more preferably, about 0.07, 0.35, 0.7, or 1.4 g/day.

Structure of natural analogues of occidiofungin is provided by Formula I (also provided in FIG. 1):

Occidiofungin A: $R_1$ = H, $R_2$ = H, $R_3$ = H or (CO)CH$_2$CH$_2$CH$_2$C≡CH,
Occidiofungin B: $R_1$ = OH, $R_2$ = H, $R_3$ = H or (CO)CH$_2$CH$_2$CH$_2$C≡CH,
Occidiofungin C: $R_1$ = H, $R_2$ = Cl, $R_3$ = H or (CO)CH$_2$CH$_2$CH$_2$C≡CH, or
Occidiofungin D: $R_1$ = OH, $R_2$ = Cl, $R_3$ = H or (CO)CH$_2$CH$_2$CH$_2$C≡CH.

As seen in Formula I, natural analogues of occidiofungin are composed of eight amino acids. One of these amino acids is NAA, which contains a xylose sugar. NAA is 3 amino-5,6-dihydroxy-7-O-xylose-octadecanoic acid. The carbon atoms in NAA are numbered based on the carbonyl group of NAA as the first carbon (FIG. 1). Also, the fifth and sixth carbon atoms of NAA each have a hydroxyl group. The seventh carbon of NAA is connected to a xylose via an ether linkage and a $C_{11}H_{23}$ moiety. Certain structure and sequence information of occidiofungin is disclosed in United States patent application publication number 2011/0136729, which is herein incorporated by reference in its entirety. Certain embodiments of the instant invention provide OF-Δxyl analogues and methods of making OF-Δxyl analogues.

Figure 2A:
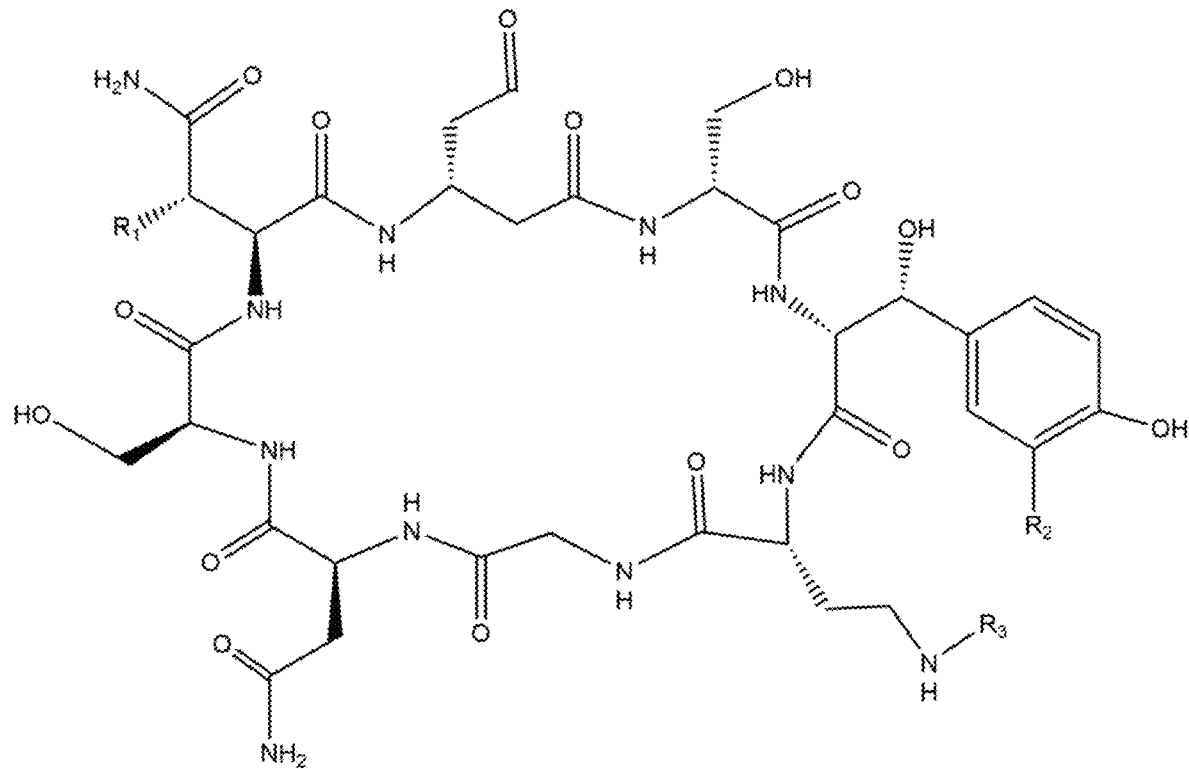
FIGS. 2A-2D. A, B, C and D provide the structures of aldehyde, amine, triazole and hydrazone containing OF-Δxyl analogues, respectively.

In one embodiment, an OF-Δxyl analogue comprises an aldehyde group, wherein the fifth carbon of NAA is the carbonyl group of the aldehyde, while the part of NAA from the sixth carbon is removed from the parent occidiofungin. Such OF-Δxyl analogue is referred to as aldehyde containing OF-Δxyl analogue and it can be represented by Formula II (also provided in FIG. 2A).

[Chemical structure of Occidiofungin parent compound]

Occidiofungin A: R$_1$ = H, R$_2$ = H, R$_3$ = H or (CO)CH$_2$CH$_2$CH$_2$C≡CH,
Occidiofungin B: R$_1$ = OH, R$_2$ = H, R$_3$ = H or (CO)CH$_2$CH$_2$CH$_2$C≡CH,
Occidiofungin C: R$_1$ = H, R$_2$ = Cl, R$_3$ = H or (CO)CH$_2$CH$_2$CH$_2$C≡CH, or
Occidiofungin D: R$_1$ = OH, R$_2$ = Cl, R$_3$ = H or (CO)CH$_2$CH$_2$CH$_2$C≡CH.

In another embodiment, the carbonyl carbon of the aldehyde containing OF-Δxyl analogue is aminated to produce an analogue containing an amine group. Therefore, in such embodiments, the fifth carbon of NAA is connected to an amine group while the part of NAA beyond the sixth carbon is removed from the parent occidiofungin. Such OF-Δxyl analogue is referred to as amine containing OF-Δxyl analogue and can be represented by Formula III (also provided in FIG. 2B).

[Chemical structure of amine containing OF-Δxyl analogue]

Occidiofungin A: R$_1$ = H, R$_2$ = H, R$_3$ = H or (CO)CH$_2$CH$_2$CH$_2$C≡CH,
Occidiofungin B: R$_1$ = OH, R$_2$ = H, R$_3$ = H or (CO)CH$_2$CH$_2$CH$_2$C≡CH,
Occidiofungin C: R$_1$ = H, R$_2$ = Cl, R$_3$ = H or (CO)CH$_2$CH$_2$CH$_2$C≡CH, or
Occidiofungin D: R$_1$ = OH, R$_2$ = Cl, R$_3$ = H or (CO)CH$_2$CH$_2$CH$_2$C≡CH.

R$_4$ and R$_5$ in an amine containing OF-Δxyl analogue can be H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen.

In certain embodiment, the aldehyde containing OF-Δxyl analogues can be further modified to produce a triazole containing OF-Δxyl analogue. In such embodiment, the fifth carbon of NAA is connected to a triazole ring, while the part of NAA from the sixth carbon and beyond is removed from the parent occidiofungin. Such OF-Δxyl analogue is referred to as triazole containing OF-Δxyl analogue and can be represented by Formula IV (also provided in FIG. 2C).

[Chemical structure of triazole containing OF-Δxyl analogue]

Occidiofungin A: R$_1$ = H, R$_2$ = H, R$_3$ = H or (CO)CH$_2$CH$_2$CH$_2$C≡CH,
Occidiofungin B: R$_1$ = OH, R$_2$ = H, R$_3$ = H or (CO)CH$_2$CH$_2$CH$_2$C≡CH,
Occidiofungin C: R$_1$ = H, R$_2$ = Cl, R$_3$ = H or (CO)CH$_2$CH$_2$CH$_2$C≡CH, or
Occidiofungin D: R$_1$ = OH, R$_2$ = Cl, R$_3$ = H or (CO)CH$_2$CH$_2$CH$_2$C≡CH.

In certain embodiments, the aldehyde containing OF-Δxyl analogues can be further modified to produce a hydrazone containing OF-Δxyl analogue. In such embodiment, the fifth carbon of NAA is connected to a hydrazine group, while the part of NAA from the sixth carbon and beyond is removed from the parent occidiofungin. Such OF-Δxyl analogue is referred to as a hydrazone containing OF-Δxyl analogue and can be represented by Formula V (also provided in FIG. 2D).

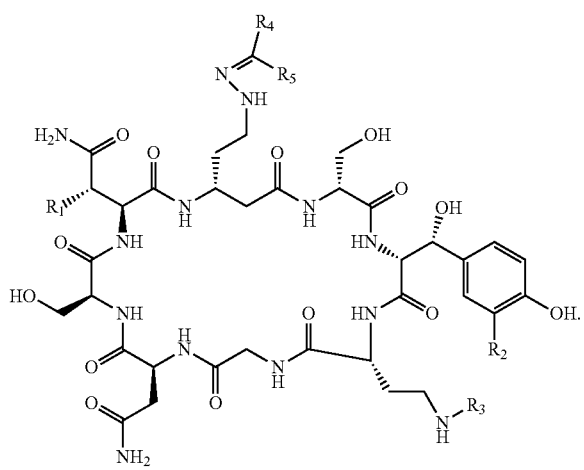

Occidiofungin A: $R_1$ = H, $R_2$ = H, $R_3$ = H or (CO)CH$_2$CH$_2$CH$_2$C≡CH,
Occidiofungin B: $R_1$ = OH, $R_2$ = H, $R_3$ = H or (CO)CH$_2$CH$_2$CH$_2$C≡CH,
Occidiofungin C: $R_1$ = H, $R_2$ = Cl, $R_3$ = H or (CO)CH$_2$CH$_2$CH$_2$C≡CH,
or
Occidiofungin D: $R_1$ = OH, $R_2$ = Cl, $R_3$ = H or (CO)CH$_2$CH$_2$CH$_2$C≡CH.

Certain embodiments of the invention provide methods for producing an aldehyde containing OF-Δxyl analogue. Such methods comprise oxidative cleavage of NAA of a natural occidiofungin between the fifth and sixth carbons while converting the fifth carbon to a carbonyl of the resulting aldehyde. Therefore, after an oxidative cleavage reaction, occidiofungin of Formula I is converted into an OF-Δxyl analogue of Formula II.

"Oxidative cleavage" as used herein comprises treating an occidiofungin of Formula I with appropriate reagents under appropriate conditions to cleave the carbon-carbon bond between the fifth and the sixth carbons of NAA, and carbonyl group is formed on the fifth carbon and optionally, on the sixth carbon.

In some embodiments, NAA is subjected to oxidative cleavage between the fifth and sixth carbons with a metaperiodate, for example, metaperiodic acid (HIO$_4$), sodium periodate (NaIO$_4$), potassium periodate (KIO$_4$), or a permanganate salt, such as KMnO4. In certain embodiments, oxidative cleavage between the fifth and sixth carbons with a periodate is performed on carbohydrates in water. In specific embodiments, oxidative cleavage between the fifth and sixth carbons is performed with a periodate in mixed aqueous organic solvents, such as acetonitrile/water, water/methanol and water/isopropanol. A skilled artisan can determine an appropriate ratio of water and the organic solvent.

Figure 3A:
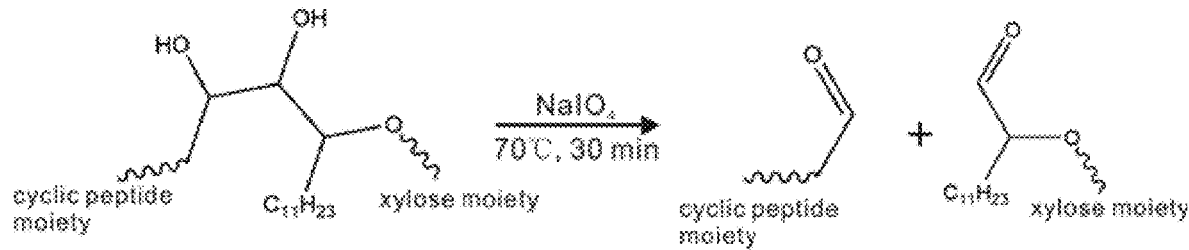
FIGS. 3A-3E. A provides a scheme of oxidative cleavage for the synthesis of aldehyde containing OF-Δxyl analogues, B describes reductive amination for the synthesis of amine containing OF-Δxyl analogues, C provides a scheme for the synthesis of triazole containing OF-Δxyl analogues and D describes a scheme for the synthesis of hydrazone containing OF-Δxyl analogues, E describes a scheme for synthesis of three acyl lipid analogs.

Oxidative cleavage reaction with periodate converts the fifth as well as the sixth carbons of NAA to carbonyl groups (FIG. 3A). Additional examples of periodates useful in such oxidative cleavage are known to a skilled artisan and such embodiments are within the purview of the invention.

In a specific embodiment, an occidiofungin of Formula I is incubated with NaIO$_4$ for about 20-40 minutes at about 60-80° C. to produce an aldehyde containing OF-Δxyl analogue of Formula II (FIG. 3A). The product can be further purified, for example, via column chromatography, such as HPLC.

Additional reactions designed to cleave the NAA between the fifth and sixth carbons while converting the fifth carbon to a carbonyl group are known in the art and such embodiments are within the purview of the invention.

Figure 2B:
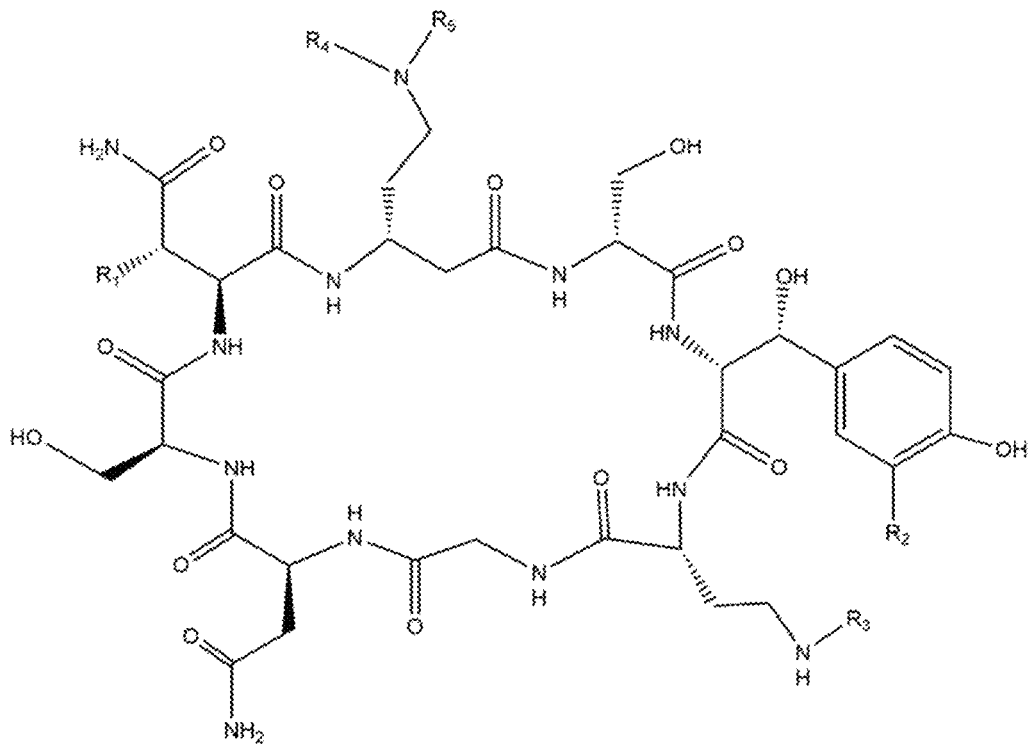
Figure 2C:
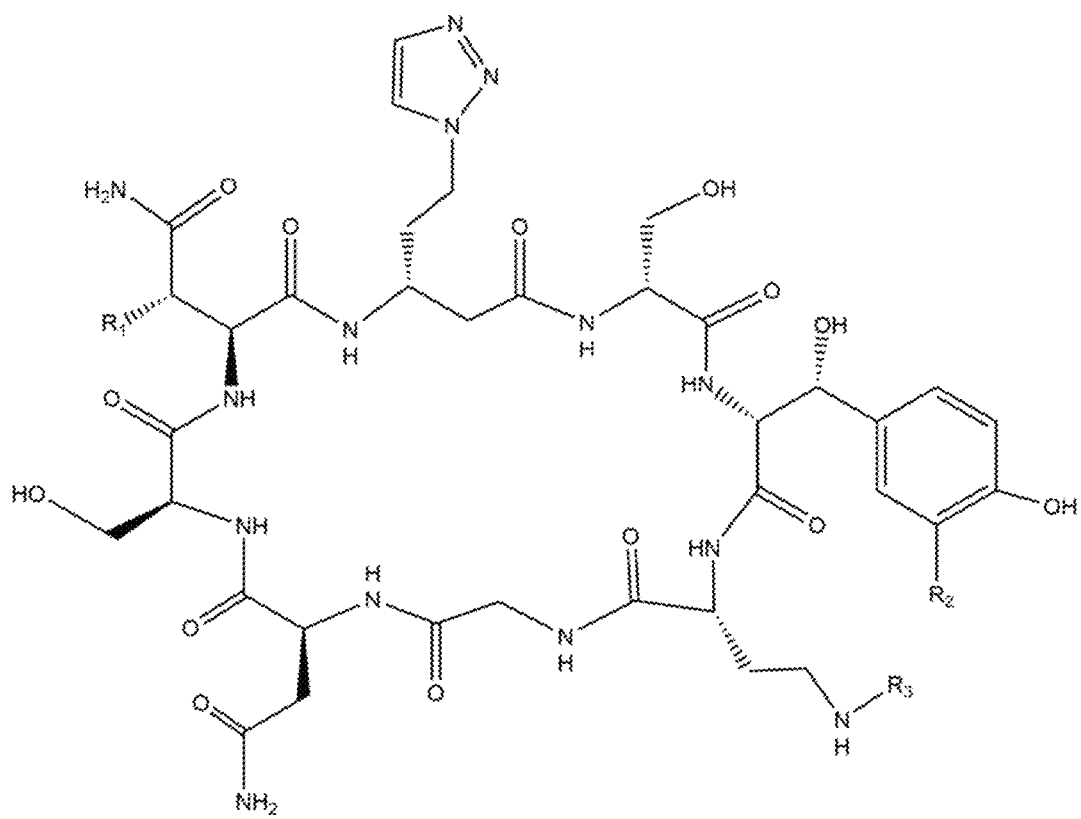
Figure 3B:
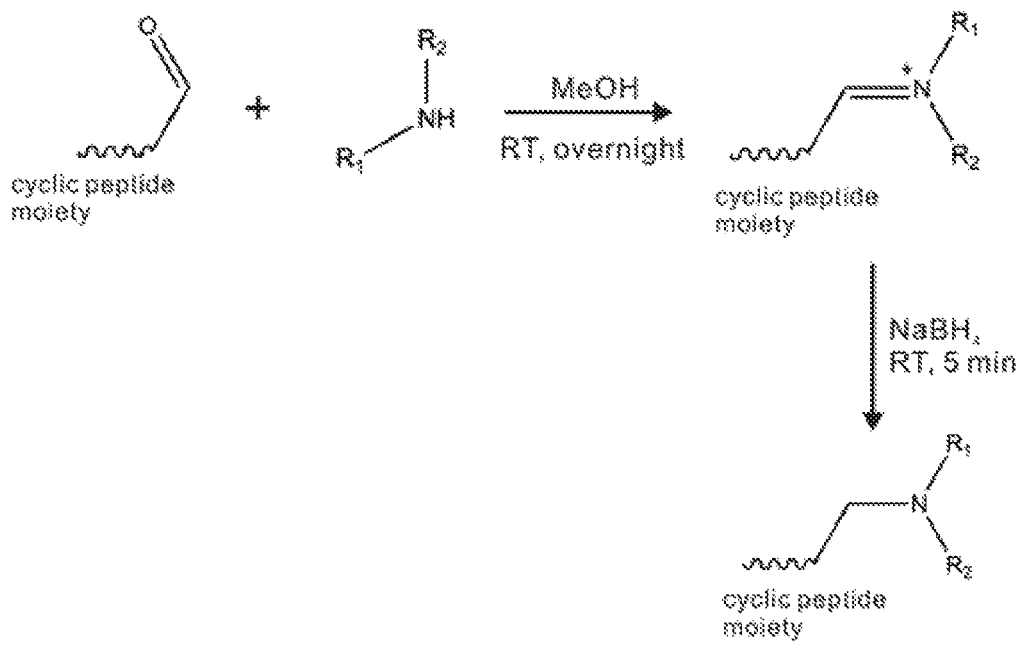

Further embodiments of the invention also provide methods for producing amine containing OF-Δxyl analogue (FIG. 2B). In certain such embodiments, an amine containing OF-Δxyl analogue is produced from an aldehyde containing OF-Δxyl analogue. For example, an aldehyde containing OF-Δxyl analogue is subject to a reductive amination with a primary or secondary amine to produce an amine containing OF-Δxyl analogue. This is a two-step reaction, with a first step involving an imine formation with an alcohol, such as MeOH, followed by reduction, for example, with NaBH$_4$ (FIG. 3B). Amines suitable for reductive amination include undecylamine, dodecylamine and DL-dihydrosphingosine.

Additional reactions suitable for converting aldehyde containing OF-Δxyl analogue to amine containing OF-Δxyl analogue are well known to a person skilled in the art and such embodiments are within the purview of the invention.

Further embodiments of the invention provide modifying amine containing OF-Δxyl analogues, particularly, at $R_4$ and $R_5$ positions of Formula III. For example, $R_4$ and $R_5$ in Formula III can be H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen. A skilled artisan can design reactions for converting amine containing OF-Δxyl analogues to corresponding analogues containing such substitutions and such embodiments are within the purview of the invention.

Figure 2D:
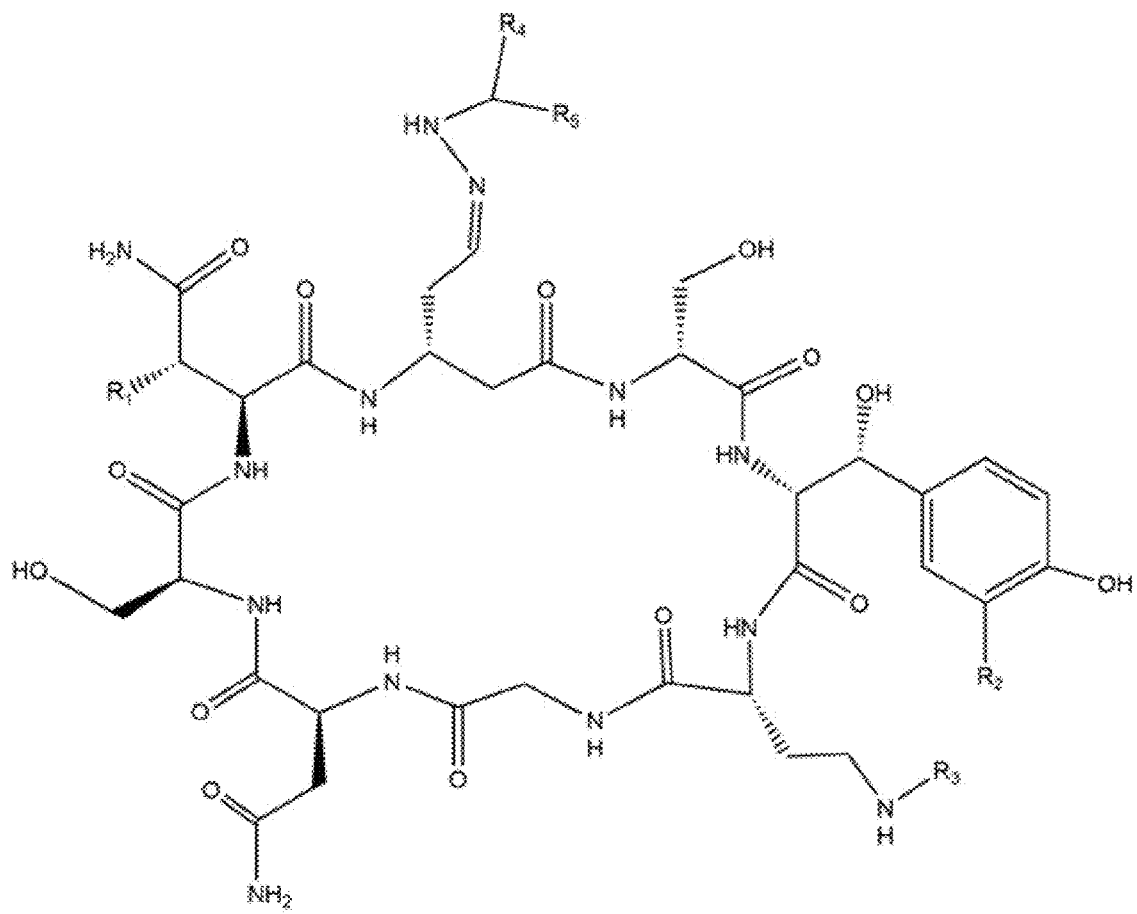
Figure 3C:
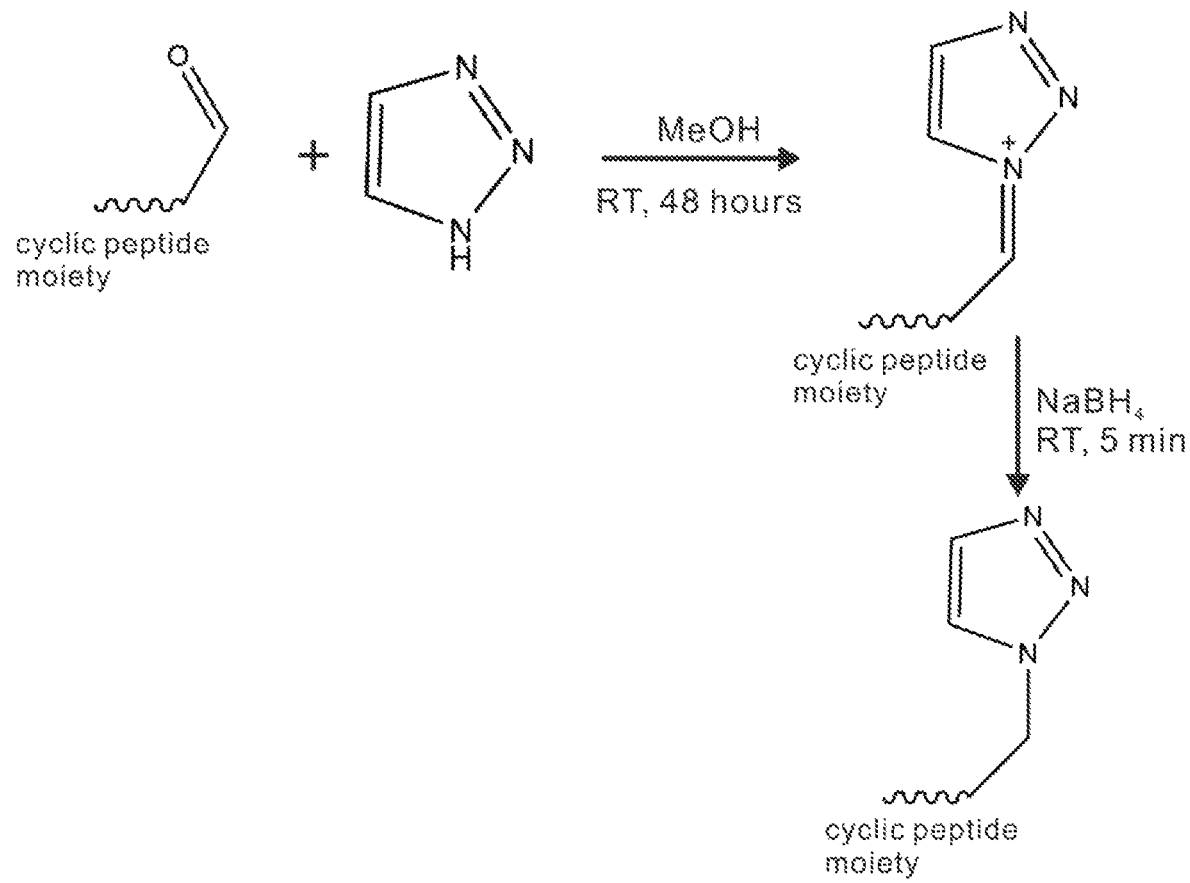

Further embodiments of the invention also provide methods for producing hydrazone containing OF-Δxyl analogue of Formula V (FIG. 2D). An example of such reaction is provided in FIG. 3C. In this reaction, an aldehyde containing OF-Δxyl analogue is incubated with an alcohol, for example, methanol, at an appropriate temperature, for example, about 20 to 35° C., preferably, about 25° C., for about 40 to 60 hours, preferably, about 50 hours, even more preferably, about 48 hours. This reaction produces an intermediate OF-Δxyl analogue, which is reduced with an appropriate reducing agent, for example, with NaBH$_4$ (FIG. 3C). Triazole moiety illustrated in FIG. 3C can be substituted or unsubstituted on one or more positions, for example, by OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen.

Figure 3D:
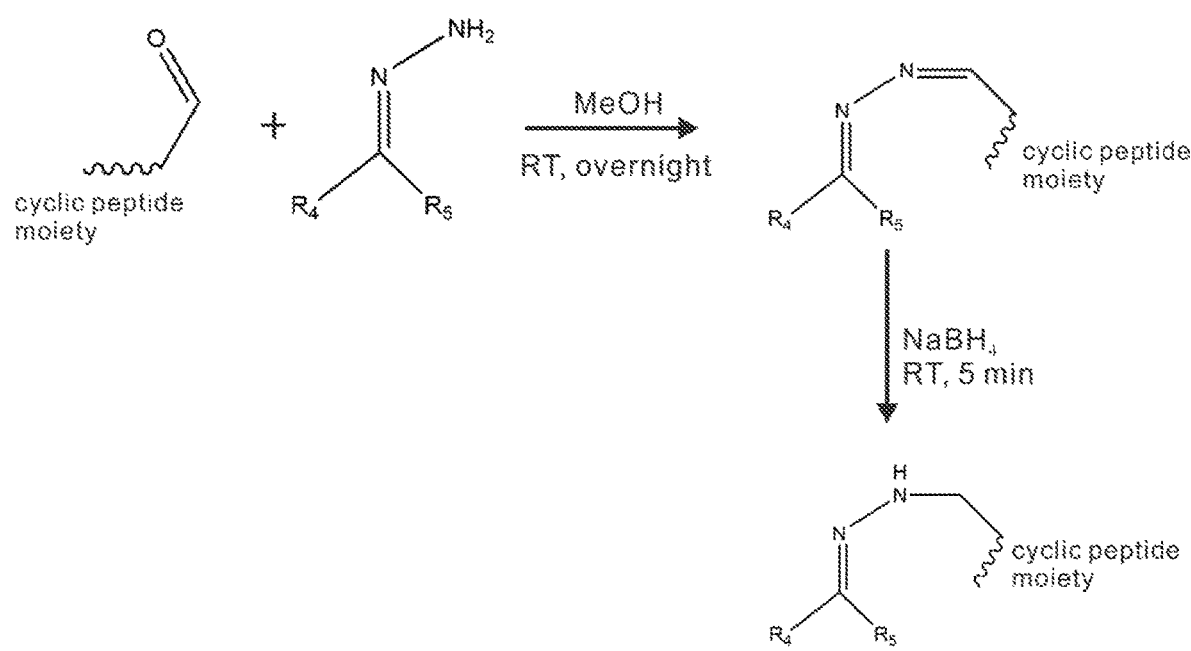

Even further embodiments of the invention also provide methods for producing hydrazone containing OF-Δxyl analogue of Formula V (FIG. 2D). In certain embodiments, a hydrazone containing OF-Δxyl analogue is produced from an aldehyde containing OF-Δxyl analogue. An example of such reaction is provided in FIG. 3D. In this reaction, an aldehyde containing OF-Δxyl analogue is incubated with an alcohol, for example, methanol, at an appropriate temperature, for example, about 20 to 35° C., preferably, about 25° C., for about 10 to 20 hours, preferably, about 15 hours, even more preferably, about 12 hours. This reaction produces an intermediate OF-Δxyl analogue, which is reduced with an appropriate reducing agent, for example, with NaBH$_4$ (FIG. 3D). $R_4$ or $R_5$ in FIG. 3D can be independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen.

In certain such embodiments, an aldehyde containing OF-Δxyl analogue is treated with certain hydrazines, for example, phenyl hydrazine, 2-nitrophenyl hydrazine, 4-nitrophenyl hydrazine or 2,4-dinitrophenyl hydrazine. In certain such embodiments, an appropriate hydrazine is dissolved in an aqueous organic reaction mixture in the presence of a suitable Bronsted acid or base or a suitable Lewis acid or base to produce hydrazine containing OF-Δxyl analogues. Aqueous organic reaction mixtures suitable in such embodiments include mixtures of acetonitrile/water, water/methanol and water/isopropanol. A skilled artisan can determine an appropriate ratio of water and the organic solvent. Accordingly, under certain embodiments $R_6$ group of Formula V can be phenyl, 2-nitrophenyl, 4-nitrophenyl or 2,4-dinitrophenyl.

When present, the nitro-groups on the hydrazone containing OF-Δxyl analogues, for example, analogs made from 2-nitrophenyl hydrazine, 4-nitrophenyl hydrazine or 2,4-dinitrophenyl hydrazine, can be further reduced to amines, which in turn could be further modified. For example, the resulting aromatic amines can be subjected to reductive amination with a variety of aliphatic or aromatic aldehydes, such as acetaldehyde, linear chain aldehydes, branched chain alkyl aldehydes and benzaldehyde. Additional modifications include conjugation to OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted hetero- cycle, substituted or unsubstituted ether, substituted or unsubstituted thioether, substituted or unsubstituted ketone or a halogen. A skilled artisan can design reactions for converting amines from reduced hydrazone containing OF-Δxyl analogues to corresponding analogues containing such substitutions and such embodiments are within the purview of the invention.

Salts of Occidiofungin Analogues of the Invention

In some embodiments the subject invention provides salts of the OF-Δxyl analogues described herein. The salts can be a salt with an inorganic acid, such as hydrochloric acid, hydrobromic acid, perchloric acid, nitric acid, thiocyanic acid, sulfuric acid, and phosphoric acid; an organic acid, such as trifluoroacetic acid (TFA), formic acid, acetic acid, propionic acid, glycolic acid, lactic acid, pyruvic acid, oxalic acid, malonic acid, succinic acid, maleic acid, and fumaric acid; or a salt with a base, such as sodium hydroxide, ammonium hydroxide, potassium hydroxide, and organic bases such as mono-, di-, trialkyl and aryl amines, and substituted ethanolamines.

Further salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-di sulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent occidiofungin analogue is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the occidiofungin analogues contains a basic functionality, salts of non-toxic organic or inorganic acids, such as hydrochloride, hydrobromide, tartrate, mesylate, acetate, maleate, oxalate and the like.

Certain embodiments provide amorphous forms of salts of the OF-Δxyl analogues disclosed herein. Such amorphous forms are advantageous for oral, pulmonary, buccal, suppository delivery.

Routes of Administration and Dosage Forms

In certain embodiments, the OF-Δxyl analogues can be administered intramuscularly, subcutaneously, intrathecally, intravenously or intraperitoneally by infusion or injection. Solutions of the occidiofungin analogues can be prepared in water, optionally mixed with a nontoxic surfactant. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the occidiofungin analogues that are adapted for the extemporaneous preparation of sterile injectable or infusible solutions or dispersions, optionally encapsulated in liposomes. Preferably, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained by, for example, the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating the OF-Δxyl analogues in the required amount in the appropriate solvent as described herein with various of the other ingredients enumerated herein, as required, preferably followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

The compositions of the subject invention may also be administered orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the subject's diet.

For oral therapeutic administration, the OF-Δxyl analogues can be combined with one or more excipients and used in the form of ingestible tablets, buccal tablets, troches, capsules, elixirs, suspensions, syrups, wafers, and the like. Such compositions and preparations should contain at least 0.1% of a occidiofungin analogue of the present invention. The percentage of the occidiofungin analogues of the invention present in such compositions and preparations may, of course, be varied and may conveniently be between about 2% to about 60% of the weight of a given unit dosage form. The amount of the OF-Δxyl analogues in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added.

When the unit dosage form is a capsule, it may contain, in addition to materials of the above type, a liquid carrier, such as a vegetable oil or a polyethylene glycol.

Various other materials may be present as coatings or for otherwise modifying the physical form of the solid unit dosage form. For instance, tablets, pills, or capsules may be coated with gelatin, wax, shellac, or sugar, and the like. A syrup or elixir may contain the an occidiofungin analogue, sucrose or fructose as a sweetening agent, methyl and propylparabens as preservatives, a dye, and flavoring such as cherry or orange flavor.

Of course, any material used in preparing any unit dosage form should be pharmaceutically acceptable and substantially non-toxic in the amounts employed.

In addition, the OF-Δxyl analogues may be incorporated into sustained-release preparations and devices. For example, the occidiofungin analogues may be incorporated into time release capsules, time release tablets, time release pills, and time release occidiofungin analogues or nanoparticles.

Pharmaceutical compositions for topical administration of the OF-Δxyl analogues to the epidermis (mucosal or cutaneous surfaces) can be formulated as ointments, creams, lotions, gels, or as a transdermal patch. Such transdermal patches can contain penetration enhancers such as linalool, carvacrol, thymol, citral, menthol, t-anethole, and the like. Ointments and creams can, for example, include an aqueous or oily base with the addition of suitable thickening agents, gelling agents, colorants, and the like. Lotions and creams can include an aqueous or oily base and typically also contain one or more emulsifying agents, stabilizing agents, dispersing agents, suspending agents, thickening agents, coloring agents, and the like. Gels preferably include an aqueous carrier base and include a gelling agent such as cross-linked polyacrylic acid polymer, a derivatized polysaccharide (e.g., carboxymethyl cellulose), and the like.

Pharmaceutical compositions suitable for topical administration in the mouth (e.g., buccal or sublingual administration) include lozenges comprising the composition in a flavored base, such as sucrose, acacia, or tragacanth; pastilles comprising the composition in an inert base such as gelatin and glycerin or sucrose and acacia; and mouthwashes comprising the active ingredient in a suitable liquid carrier. The pharmaceutical compositions for topical administration in the mouth can include penetration enhancing agents, if desired.

Useful solid carriers include finely divided solids such as talc, clay, microcrystalline cellulose, silica, alumina, and the like. Other solid carriers include nontoxic polymeric nanoparticles or microparticles. Useful liquid carriers include water, alcohols, or glycols, or water/alcohol/glycol blends, in which the occidiofungin analogues can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the OF-Δxyl analogues to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

The concentration of the OF-Δxyl analogues of the invention in such formulations can vary widely depending on the nature of formulation and intended route of administration. For example, the concentration of the occidiofungin analogues in a liquid composition, such as a lotion, can preferably be from about 0.1-25% by weight, or, more preferably, from about 0.5-10% by weight. The concentration in a semi-solid or solid composition such as a gel or a powder can preferably be about 0.1-5% by weight, or, more preferably, about 0.5-2.5% by weight.

Pharmaceutical compositions for spinal administration or injection into amniotic fluid can be provided in unit dose form in ampoules, pre-filled syringes, small volume infusion, or in multi-dose containers, and can include an added preservative. The compositions for parenteral administration can be suspensions, solutions, or emulsions, and can contain excipients such as suspending agents, stabilizing agents, and dispersing agents.

A pharmaceutical composition suitable for rectal administration comprises OF-Δxyl analogues of the present invention in combination with a solid or semisolid (e.g., cream or paste) carrier or vehicle. For example, such rectal compositions can be provided as unit dose suppositories. Suitable carriers or vehicles include cocoa butter and other materials commonly used in the art.

According to one embodiment, pharmaceutical compositions of the present invention suitable for vaginal administration are provided as pessaries, tampons, creams, gels, pastes, foams, or sprays containing an occidiofungin analogue of the invention in combination with carriers as are known in the art. Alternatively, compositions suitable for vaginal administration can be delivered in a liquid or solid dosage form.

Pharmaceutical compositions suitable for intra-nasal administration are also encompassed by the present invention. Such intra-nasal compositions comprise an occidiofungin analogue of the invention in a vehicle and suitable administration device to deliver a liquid spray, dispersible powder, or drops. Drops may be formulated with an aqueous or non-aqueous base also comprising one or more dispersing agents, solubilizing agents, or suspending agents. Liquid sprays are conveniently delivered from a pressurized pack, an insufflator, a nebulizer, or other convenient means of delivering an aerosol comprising an occidiofungin analogue. Pressurized packs comprise a suitable propellant such as dichlorodifluoromethane, trichlorofluoromethane, dichlorotetrafluoroethane, carbon dioxide, or other suitable gas as is well known in the art. Aerosol dosages can be controlled by providing a valve to deliver a metered amount of an occidiofungin analogue.

The OF-Δxyl analogues may be combined with an inert powdered carrier and inhaled by the subject or insufflated.

Pharmaceutical compositions for administration by inhalation or insufflation can be provided in the form of a dry powder composition, for example, a powder mix of an occidiofungin analogue and a suitable powder base such as lactose or starch. Such powder composition can be provided in unit dosage form, for example, in capsules, cartridges, gelatin packs, or blister packs, from which the powder can be administered with the aid of an inhalator or insufflator.

The exact amount (effective dose) of the OF-Δxyl analogues varies from subject to subject, depending on, for example, the species, age, weight, and general or clinical condition of the subject, the severity or mechanism of any infection being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an effective dose can be estimated initially either via in vivo assays or in suitable animal models. The animal model may also be used to determine the appropriate concentration ranges and routes of administration. Such information can then be used to determine useful doses and routes for administration in humans. Methods for the extrapolation of effective dosages in mice and other animals to humans are known to the art; for example, see U.S. Pat. No. 4,938,949, which is hereby incorporated by reference. A therapeutic dose can also be selected by analogy to dosages for comparable therapeutic agents.

The particular mode of administration and the dosage regimen can be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose can be in the range of from about 0.001 to about 100 mg/kg of body weight per day, preferably from about 0.01 to about 100 mg/kg of body weight per day, more preferably, from about 0.1 to about 50 mg/kg of body weight per day, or even more preferred, in a range of from about 1 to about 10 mg/kg of body weight per day. For example, a suitable dose may be about 1 mg/kg, 10 mg/kg, or 50 mg/kg of body weight per day.

The OF-Δxyl analogues can be conveniently administered in unit dosage form, containing for example, about 0.05 to about 10000 mg, about 0.5 to about 10000 mg, about 5 to about 1000 mg, or about 50 to about 500 mg of active ingredient per unit dosage form.

The OF-Δxyl analogues can be administered to achieve peak plasma concentrations of, for example, from about 0.25 to about 200 μM, about 0.5 to about 75 μM, about 1 to about 50 μM, about 2 to about 30 μM, or about 5 to about 25 μM. Exemplary desirable plasma concentrations include at least 0.25, 0.5, 1, 5, 10, 25, 50, 75, 100 or 200 μM. For example, plasma levels may be from about 1 to about 100 micromolar or from about 10 to about 25 micromolar. This may be achieved, for example, by the intravenous injection of a 0.05 to 5% solution of an OF-Δxyl analogue, optionally in saline, or orally administered as a bolus containing about 1 to about 100 mg of the OF-Δxyl analogue. Desirable blood levels may be maintained by continuous or intermittent infusion.

The OF-Δxyl analogues can be included in the compositions within a therapeutically useful and effective concentration range, as determined by routine methods that are well known in the medical and pharmaceutical arts. For example, a typical composition can include one or more of the OF-Δxyl analogues at a concentration in the range of at least about 1 mg/ml, preferably at least about 4 mg/ml, more preferably at least 5 mg/ml and most preferably at least 6 mg/ml.

The OF-Δxyl analogues may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

Optionally, the pharmaceutical compositions of the present invention can include one or more other therapeutic agents, e.g., as a combination therapy. The additional therapeutic agent(s) will be included in the compositions within a therapeutically useful and effective concentration range, as determined by routine methods that are well known in the medical and pharmaceutical arts. The concentration of any particular additional therapeutic agent may be in the same range as is typical for use of that agent as a monotherapy, or the concentration may be lower than a typical monotherapy concentration if there is a synergy when combined with an occidiofungin analogue of the present invention.

Methods of Treatment

As discussed above, the OF-Δxyl analogues disclosed herein exhibit anti-fungal activity, particularly, against *Candida* spp. Accordingly, certain embodiments of the invention provide methods of administering an OF-Δxyl analogue to a subject in need thereof to treat or prevent an infection, particularly, a fungal infection, more particularly, a yeast infection, and even more particularly, a *Candida* infection. In specific embodiments, the invention provides methods of treating or preventing an infection caused by a fungus selected from *Trichophyton mentagrophytes, Trichophyton rubrum, Rhizopus microspores, Mucor circinelloides, Mucor fragilis, Fusarium solani, Fusarium oxysporum, Aspergillus flavus, Aspergillus fumigatus, Candida albicans, Candida glabrata, Candida krusei, Candida krusei, Candida parapsilosis, Candida tropicalis* or *Cryptococcus neoformans*. Particularly, methods are provided for treating or preventing an infection with any strain listed in Table 8.

Methods for treating or preventing an infection can be performed in any subject, such as a mammal, including humans. Such methods comprise administering to a subject in need of such prevention or treatment of an infection an effective amount of an OF-Δxyl analogue the subject invention. An OF-Δxyl analogue can be administered in the form of a pharmaceutical composition of an OF-Δxyl analogue.

Preferably, an occidiofungin analogue is administered parenterally or enterally. Even more preferably, an occidiofungin analogue is administered intravaginally, intraperitoneally, subcutaneously or intravenously. The dosage of the effective amount of an occidiofungin analogue can vary depending upon the age and condition of each subject to be treated. However, suitable unit dosages typically range from about 0.01 to about 100 mg. For example, a unit dose can be in the range of about 0.2 mg to about 50 mg. Such a unit dose can be administered more than once a day, e.g., two or three times a day.

Materials and Methods

Occidiofungin was purified as previously described by Lu et al. Purified rabbit skeletal muscle filamentous actin (AKF99) was purchased from Cytoskeleton Inc. (Denver, CO). Sodium periodate (311448-5G), sodium borohydride (452882), undecylamine (94200-10ML), dodecylamine (325163-5ML), and DL-dihydrosphingosine (D6783-10MG) were purchased from Sigma (St. Louis, MO).
Synthesis of Occidiofungin Analogs Occidiofungin was dissolved in 50% acetonitrile (ACN) with 0.1% trifluoroacetic acid (TFA) at a concentration of 1 mg/mL. Sodium periodate was dissolved in ddH$_2$O at a concentration of 1 mg/mL. Equal volumes of the two solutions were mixed thoroughly in a 10 mL centrifuge tube and was incubated at 70° C. for 30 min. One milliliter of the reaction mixture was loaded on a BioRad Duoflow chromatography system with an analytical C18 column (Agilent® ZORBAX, (Agilent Technologies, Santa Clara, CA ODS, C18, 5 µm, 4.6×250 mm). The reaction mixture was separated with an isocratic flow of 20% MeOH in water and the resulting aldehyde analog of occidiofungin eluted at approximately 9 minutes. The desired product was freeze-dried and weighed on an analytical balance (Adventurer™ Pro AV114C, Ohaus Corporation, USA).

A two-step procedure of reductive amination was used to introduce a primary or secondary amine onto the aldehyde analog. The first step of reaction involves the formation of an intermediate carbinol amine, which is then dehydrated and protonated to form an iminium ion. Subsequent reduction of this iminium ion with sodium borohydride produces an alkylated amine product. The aldehyde analog of occidiofungin was dissolved in DMSO at a concentration of 10 mg/mL. Amines used were undecylamine, dodecylamine, and DL-dihydrosphingosine. Aldehyde analog (10 µL of DMSO stock solution; 100 µg) was mixed with 10-fold excess of an amino lipid (molar ratio) in 400 µL methanol. The sample was then incubated at room temperature for at least 16 hours. Solid sodium borohydride (6 mg) was weighted on an analytical balance (Adventurer™ Pro AV114C, Ohaus Corporation, USA) and was directly transferred into the reaction mixture, mixed well, and was incubated at room temperature for 5 minutes. The reaction mixture was diluted to 1 mL with 50% ACN 0.1% TFA and was separated by HPLC using a 30-minute gradient from 90% to 20% water/ACN on the analytical C18 column. Both HPLC solvents contained 0.1% TFA. Products that eluted between 50-30% water were collected and analyzed by electrospray ionization mass spectrometry (ESI-MS) on a ThermoFisher DecaXP ion trap mass spectrometer. The yield of each sample was quantified by comparing the peak area of each analog to the peak area of a 100 µg standard of occidiofungin.
NMR Spectroscopy NMR analysis of aldehyde occidiofungin analog was performed on a 5 mM sample dissolved in dimethyl sulfoxide (DMSO)-d6. The NMR data were collected on an Avance III HD-600 with a TCI Cryoprobe and an Avance III HD-850 with a TCI Cryoprobe. The $^1$H resonances were assigned according to standard methods using COSY, TOCSY, NOESY, and $^{13}$C-HSQC experiments. NMR experiments were collected at 25° C. $^1$H chemical shifts were referenced to DMSO peak at 2.5 ppm. The TOCSY experiment was acquired with a 60 ms mixing time using the Bruker DIPSI-2 spinlock sequence. The NOESY experiment was acquired with a 400 ms mixing time. Phase sensitive indirect detection for NOESY, TOCSY, and COSY experiments was achieved using the standard Bruker pulse sequences. Peaks were assigned using NMRView.
Minimum Inhibitory Concentration Assays The minimal inhibitory concentration (MIC) is the lowest concentration of compound that inhibits the visible growth of the yeast after 24 hours of incubation. MIC assays were performed in duplicate as previously described following a modified version of the CLSI M27-A3 methods.
Actin Co-Sedimentation Assay Actin binding experiments were performed as previously described for native occidiofungin by Ravichandran et al. An Agilent 1200 front end chromatography system and a TSQ Quantum™ Access Triple Quadrupole Mass Spectrometer was used to analyze phalloidin, native occidiofungin, dodecylamine analog, and the DL-dihydrosphingosine analog binding to F-actin. Following a 10 µL injection, samples containing dodecylamine analog of occidiofungin were separated using a 15-minute water/ACN (containing 0.2% formic acid) gradient starting from 95% to 40% water on a C18 column (SinoChrom ODS-BP 5 µm, 2.1 mm×50 mm). Samples containing DL-dihydrosphingosine analog were separated on the same column through a modified water/ACN gradient starting from 95% to 56% water over 5 minutes, from 56% to 52% water over 2 minutes, followed by a linear gradient from 52% to 48% water over 1 minute. The mass spectrometer was operated in positive mode and operated using a protocol optimized for each compound. Briefly, the center mass for dodecylamine analog was 1037.66 Da and the scan width was 0.3 Da. The center mass for dihydrosphingosine analog was 1153.75 Da and the scan width was 1.0 Da. Area of each compound was measured through manual integration using Xcalibur™ Software (Thermo Fisher Scientific). The standard curves were generated for each compound following the extraction protocol described above. Native occidiofungin served as the internal standard for all analogs. The $R^2$ values for each standard curve exceeded 0.98.
Actin Polymerization and Depolymerization Assay Actin polymerization and depolymerization assays were performed using the Actin polymerization biochem kit (#BK003; Cytoskeleton, Inc. Denver, CO) following the manufacturer's instructions with some modifications. Briefly, for the polymerization assay, G-actin stock solution was made at 0.2 mg/mL instead of 0.4 mg/mL. For the depolymerization assay, F-actin stock solution was diluted 9-fold instead of 5-fold. Test compounds include phalloidin, dihydrosphingosine analog, and native occidiofungin, at a final concentration of 5 µM. The experiments were done in duplicate.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Synthesis of Semisynthetic Analogues of Occidiofungin

Occidiofungin was produced and purified as described by Lu et al. and Emrick et al. Chemicals were purchased from Sigma unless otherwise indicated. Wild-type MS14 strain and xylose transferase mutant strain used were obtained from glycerol stocks and cultured on Yeast Peptone Dextrose (YPD) agar plate or broth at 35° C. Occidiofungin was produced from these cultures and used to produce OF-Δxyl analogues as described herein.

Figure 4A:
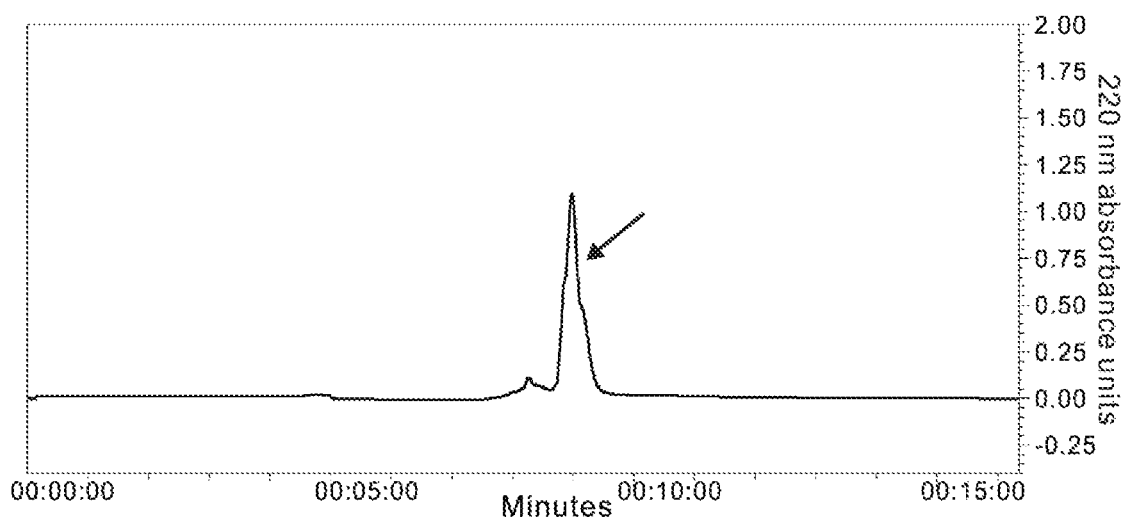
FIGS. 4A-4B. Generation and characterization of the aldehyde analog of occidiofungin. (A) HPLC isolation of the aldehyde analog of occidiofungin. The solvent used was 20% methanol in water. The black line represents the absorbance unit (AU) at 220 nm. (B) ESI-MS chromatograms of the aldehyde analog (868 Da) of occidiofungin. The data shows that the oxidative cleavage went to completion, given that there is no mass of starting material (1216 Da).

Cleavage of diols on carbons 5 and 6 of the novel amino acid yields an aldehyde containing OF-Δxyl analogue. Sodium periodate breaks apart vicinal diols to form an aldehyde containing analogue of OF-Δxyl (FIGS. 3A-3B). Occidiofungin was dissolved in 50% ACN with 0.1% TFA at a concentration of 1 mg/mL. Sodium periodate was dissolved in ddH$_2$O at a concentration of 1 mg/mL. Equal volume of the two solutions were mixed in a centrifuge tube and incubated at various temperatures from 30-70° C. for 30 min. The reaction mixture was loaded on a BioRad Duoflow™ chromatography system with an analytical column (Agilent® ZORBAX, Agilent Technologies, Santa Clara, CA ODS, C18, 5 μm, 4.6×250 mm). The reaction mixture was chromatographed with an isocratic flow of 20% MeOH in ddH$_2$O. The aldehyde containing analogue of OF-Δxyl elutes at approximately 9 minutes (FIG. 4). The desired product is dried and weighed on analytical balance (Adventurer™ Pro AV114C, Ohaus Corporation, USA). The efficiency of the reaction and recovery of the desired aldehyde-occidiofungin product was greater than 90%.

Reductive amination restores the aliphatic structural element of occidiofungin through a condensation reaction with the free amine. A two-steps procedure of reductive amination of aldehyde containing OF-Δxyl analogue (FIG. 2A) was used to introduce a primary or secondary amine at aldehyde. The first step of reaction involves the formation of an intermediate carbinol amine, which then undergoes dehydratation and protonation to form an iminium ion. Subsequent reduction of this iminium ion with sodium borohydride produces an alkylated secondary or tertiary amine product depending on the nature of the starting material.

Chemicals used produce certain OF-Δxyl analogues include undecylamine, dodecylamine, and DL-dihydrosphingosine. For example, aldehyde containing OF-Δxyl analogue is dissolved in DMSO at a concentration of 10 mg/mL and mixed with 10-fold excess of undecylamine (molar ratio) in pure methanol and was incubated at room temperature overnight. Solid sodium borohydride (6 mg) was added to the overnight reaction and incubated at room temperature for 5 minutes. The resulting product in the reaction mixtures was chromatographically purified using a linear water/ACN gradient starting from 90% to 20% water over 30-minute period. Both solvents used in the mobile phase contained 0.1% trifluoroacetic acid (TFA). The products eluted between 50-30% water with 0.1% TFA (FIG. 5). The reaction efficiencies were determined by comparing the peak area of each sample to the peak area of a 100 μg standard of occidiofungin (Table 1). The efficiency of the reactions and isolation of the desired products were greater than 50% for all reactions.

Figures 6A, 6B, 6C:
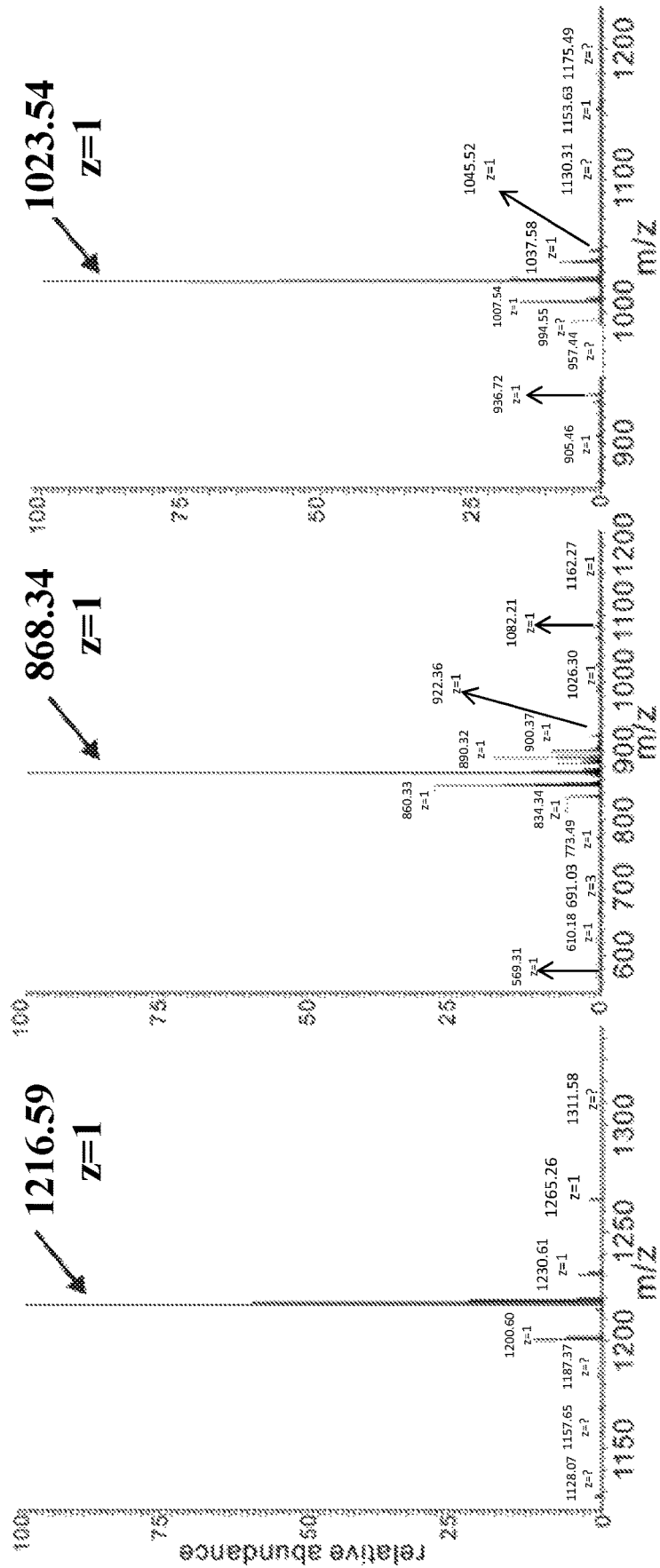
FIGS. 6A-6E. ESI-MS of OF-Δxyl analogues. (A) wild-type, (B) an aldehyde containing OF-Δxyl analogue, (C) an aldehyde containing OF-Δxyl analogue following a reaction with undecylamine, (D) an aldehyde containing OF-Δxyl analogue following a reaction with dodecylamine, and (E) an aldehyde containing OF-Δxyl analogue following a reaction with DL-dihydrosphingosine.
Figures 6D, 6E:
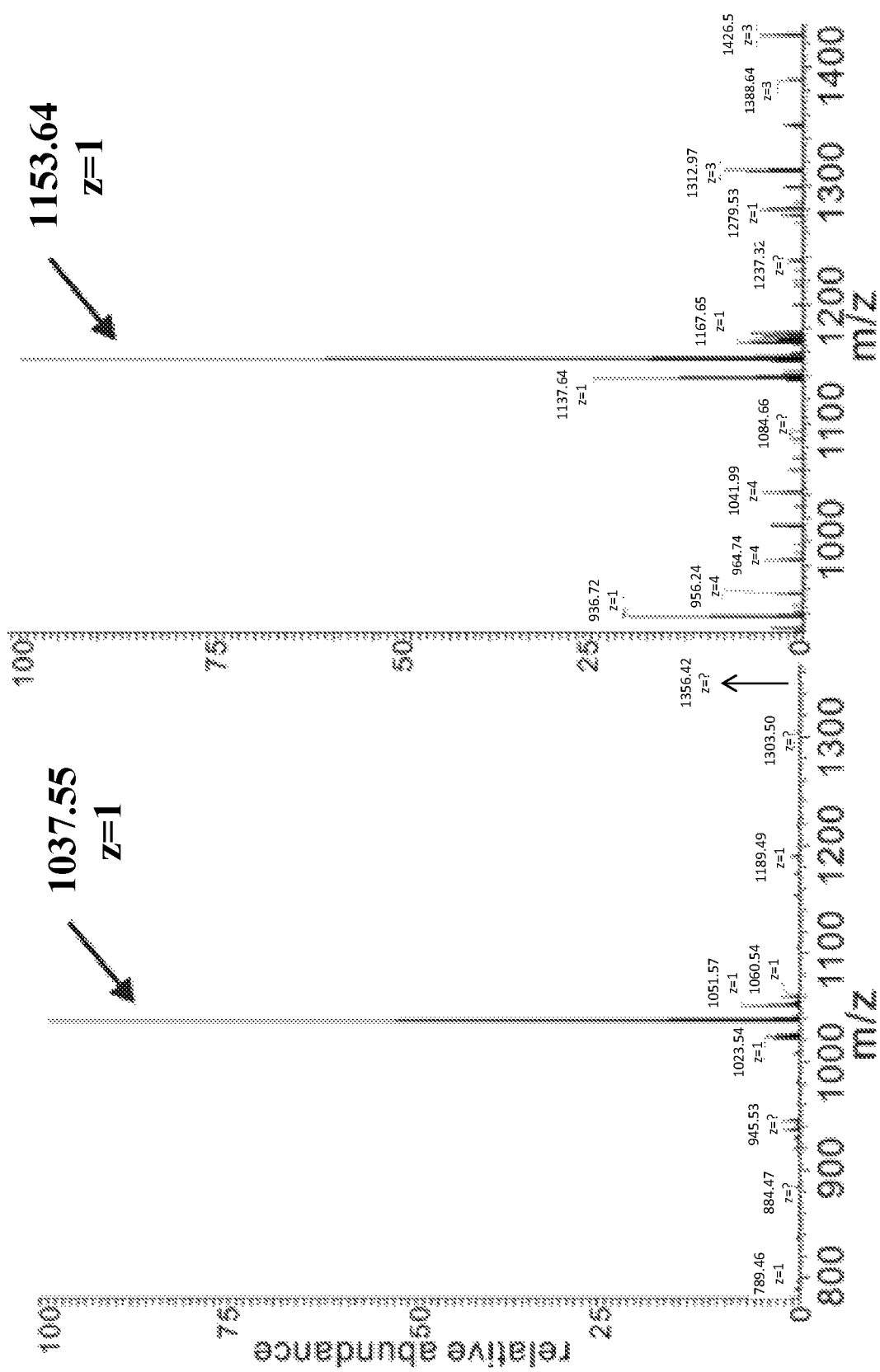

The molecular weight of the purified product was determined by electrospray ionization mass spectrometry (ESI-MS) on a ThermoFisher DecaXP ion trap mass spectrometer (Table 1). Briefly, around 1 μg of dried sample was resuspended in 100 μl of 50% ACN/water (vol/vol) and analyzed by direct infusion in positive mode. MS data were recorded in a 0.5 min time frame (FIG. 6). Occidiofungin wild-type was used as a comparison and mass spectral control. Nuclear magnetic resonance studies were done to verify the structure of the OF-Δxyl analogue.

TABLE 1

Summary of reactions. The starting material, type of reaction, and yield of reaction are shown. The products are confirmed by ESI-MS, all measured mass are the same with expected. Yield of oxidation reaction was determined based on dry weight of both starting material and product, while the yields of reductive amination reactions were based on the peak volume of both starting material and product on HPLC.

| Starting material | Type of reaction | Amine | Yield (%) | Molecular Weight (Da) Expected | Measured |
|---|---|---|---|---|---|
| wild-type | oxidation | N.A. | 90 | 868 | 868 |
| aldehyde variant | reductive amination | undecylamine | 70 | 1024 | 1024 |
| aldehyde variant | reductive amination | dodecylamine | 84 | 1038 | 1038 |
| aldehyde variant | reductive amination | DL-dihydro-sphingosine | 51 | 1154 | 1154 |

Figure 4B:
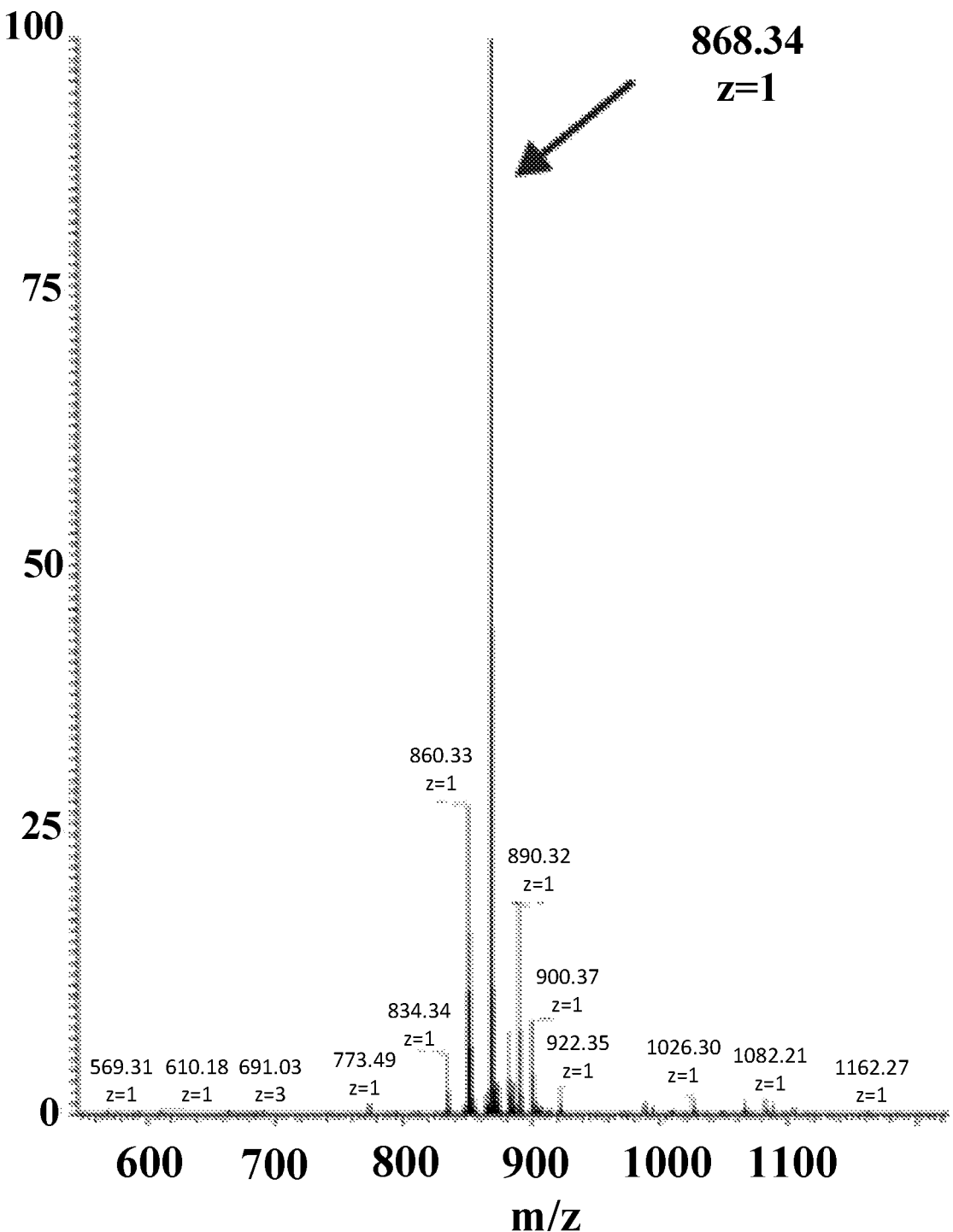
Figure 8A:
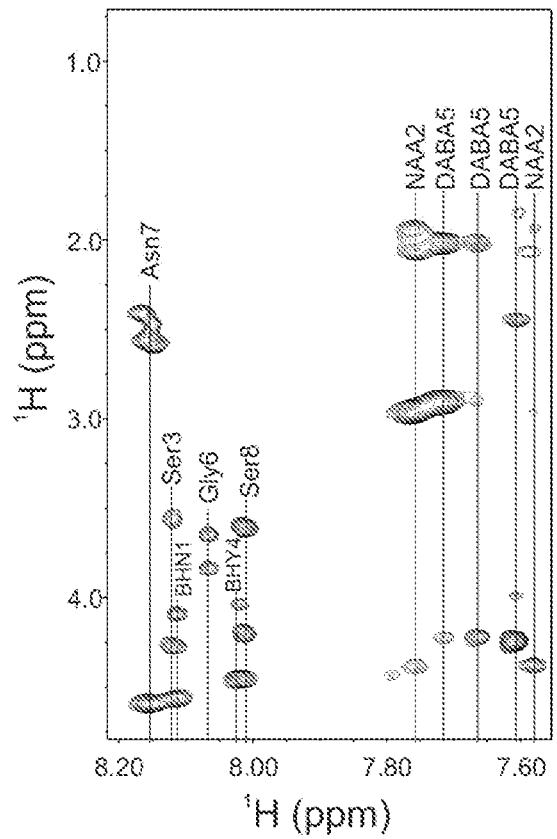
FIGS. 8A-8B. TOCSY and NOESY NMR spectra of occidiofungin. (A) TOCSY spin system correlations of the aldehyde occidiofungin product. Fingerprint region (NH correlations), alpha to side chain correlations and side chain correlations are shown. Abbreviations are: diamino butyric acid 5 (DABAS), novel amino acid 2 (NAA2), beta-hydroxy-asparagine 1 (BHN1), and beta-hydroxy-tyrosine 4 (BHY4). (B) NOESY spin system correlations. The expansion shows the intra-residue NOE interaction of the aldehyde proton of NAA2 to the amide proton of the NAA2.
Figure 8B:
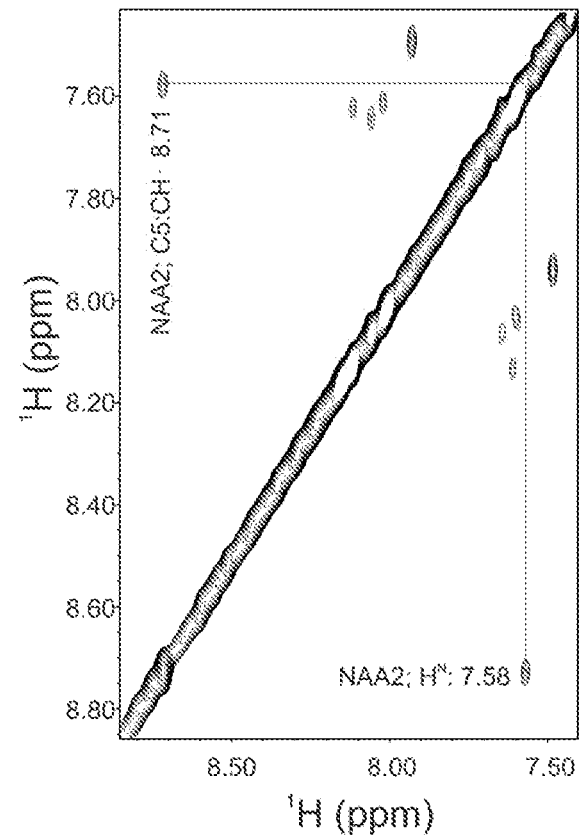

The removal of the aliphatic chain resulted in a highly polar compound (FIGS. 1-2), which was isolated by HPLC under isocratic conditions. Oxidative cleavage of the vicinal diols proceeded efficiently, and occidiofungin was completely converted to the aldehyde product (FIG. 2 and FIG. 3A). This was confirmed by mass spectrometry of the reaction mixture (FIG. 4B). The isolated aldehyde has a mass of 868 Daltons (Da). Nuclear magnetic resonance (NMR) analyses of the isolated product further confirmed the isolation of the cyclic peptide with the aldehyde on carbon 5 (C5) of the NAA2 residue. The individual amino acid spin systems in the 2D TOCSY spectra are shown in (FIG. 8A) and the chemical shifts for the aldehyde product are provided in Table 2. The through-space proton interaction between the aldehyde proton and the amide proton of the novel amino acid was observed in the 2D NOESY spectra (FIG. 8B), supporting the proton chemical shift assignments of the aldehyde product. The aldehyde occidiofungin product was subsequently used in reductive amination reactions affording the synthesis of new analogs of occidiofungin.

Figure 3E:
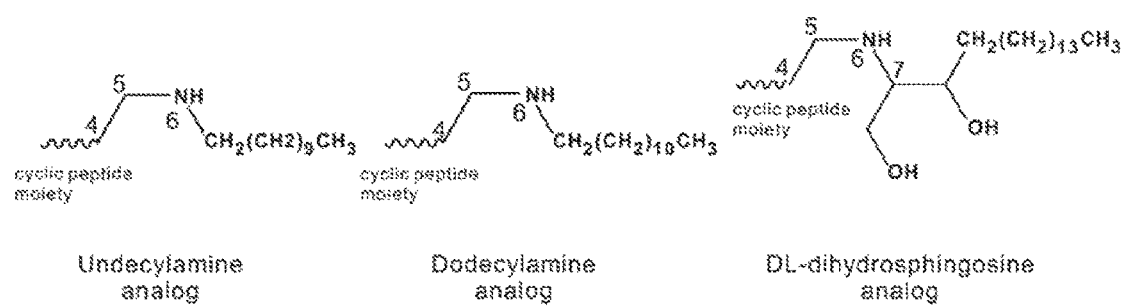

Reductive amination reactions using three commercially available long chain alkyl amines and the aldehyde occidiofungin products were performed (FIG. 3B). The oxidative cleavage of the diol in the NAA2 resulted in a loss of thirteen carbons in the aliphatic chain. Since the xylose itself is not required for the antifungal activity, undecylamine and dodecylamine were used to restore the length of the aliphatic chain. A secondary amine is incorporated at the carbon six (C6) position and an aliphatic chain of eleven and twelve carbons were introduced for the undecylamine and dodecylamine products, respectively (FIG. 3E). The alkyl amine dihydrosphingosine was chosen because a hydroxyl group would be reintroduced into the side chain near the normally occurring positions found within the native product (FIG. 3E). The unoptimized reactions were very efficient. The yield of the semisynthetic undecylamine, dodecylamine, and dihydrosphingosine analogs were 70, 80, and 50%, respectively (Table 2, FIGS. 5-6). The final undecylamine, dodecylamine, and dihydrosphingosine occidiofungin products had the expected masses of 1023.7, 1037.7, and 1153.9 Da, respectively (Table 2, FIG. 5-6).

Additional analogs can be rapidly synthesized by this approach and the structural diversity of analogs made can be expanded by the synthesis of novel amino lipid compounds that are not readily available.

TABLE 2

NMR chemical shifts for aldehyde analog of occidiofungin. Proton chemical shift values were from a TOCSY and NOESY experiments.

| Amino Acid | $H^N$ | $H^\alpha$ | $H^\beta$ | Other protons |
|---|---|---|---|---|
| BHN1 | 8.11 | 4.57 | 4.09 | β-OH: 5.68, γ-NH2: 7.20, 6.70 |
| NAA2 | 7.76 7.58 | | | C2: CH2- 2.08&1.92, C3: CH- 4.39, C4: CH2- 2.96, C5: CH- 8.71 |
| Ser3 | 8.12 | 4.27 | 3.56 | β-OH: 4.99 |
| BHY4 | 8.02 | 4.45 | 4.04 | β-OH: 5.71, OH - 9.28, C2&C6: CH - 7.16, C3&C5: CH - 6.70 |
| DABA5 | 7.61 | 4.23 | 2.02 | γ-H: 2.91, NH2: 7.71 γ-H: 2.87, NH2: 7.66 |
| Gly6 | 8.07 | 3.82, 3.64 | | |
| Asn7 | 8.16 | 4.59 | 2.58, 2.47 | γ-NH2: 7.44, 6.97 |
| Ser8 | 8.01 | 4.20 | 3.61 | β-OH: 5.08 |

Example 2—Minimum Inhibitory Concentration (Mic) of the OF-Δxyl Analogues

Minimum inhibitory concentration (MIC) susceptibility testing was performed following a modified version, as previously reported, of the CLSI M27-A3 methods for the susceptibility testing of yeasts. Incubation temperature was 35° C. and the inoculum size was 0.5-2.5×10³ colony-forming units (CFU)/mL for yeasts. MICs were performed to determine the bioactivity of each new OF-Δxyl analogue (Table 3). The minimal inhibitory concentration (MIC) is the lowest concentration of compound that inhibits the visible growth of the yeast after 24 hours of incubation and the assays were performed in duplicate. The aldehyde containing OF-Δxyl analogues with the addition of an undecylamine, dodecylamine, or DL-dihydrosphingosine did not demonstrate any inhibitory activity against C. albicans at the concentration tested. However, the addition of DL-dihydrosphingosine to the aldehyde containing OF-Δxyl analogue exhibited a low micromolar inhibitory activity against Saccharomyces cerevisiae and Candida glabrata.

The aldehyde, undecylamine, and dodecylamine analogs were inactive at concentrations 64-fold higher than the inhibitory concentration of native occidiofungin against the Candida species tested and S. cerevisiae strain tested (Table 3). The undecylamine and dodecylamine analogs have a similar aliphatic carbon length as native occidiofungin. Further, these analogs have similar polarity as native occidiofungin, as was observed by the HPLC retention times (FIGS. 5-6). The major structural differences to native compound are the conversion of a (C5)-(C6) to (C5)-(N6) bond in the side chain of NAA2, the removal of the vicinal diol group, and the loss of a xylose sugar. Dihydrosphingosine analog was synthesized to test whether the introduction of a hydroxyl group near (C6) position could restore activity. Dihydrosphingosine analog has one branched alcohol on (C7) and a hydroxyl on (C8) positions normally found within native occidiofungin. Further, the aliphatic chain of dihydrosphingosine analog is five carbons longer than the native compound. The dihydrosphingosine restores some antifungal activity as observed by a low micromolar inhibitory activity against S. cerevisiae, C. albicans, and Candida glabrata; the MICs were 2, 16, and 8 µg/mL, respectively. The loss of activity, or the reduction of activity, of the semisynthetic analogs of occidiofungin could be attributed to a reduction in their ability to penetrate the plasma membrane to reach cellular target (binding to cell envelope or inability to cross plasma membrane) or a loss in affinity to actin (the cellular target of occidiofungin).

TABLE 3

MIC (µg/ml) of occidiofungin analogues against Candida glabrata ATCC2001, Candida albicans ATCC 3147 and S. cerevisiae DGY6 haploid BY4741.

| occidiofungin analogues | Sacchaomyces cerevisiae DGY6 haploid BY4741 | Candida glabrata ATCC 2001 | Candida albicans ATCC 3147 |
|---|---|---|---|
| wild-type | 0.0625 | 0.5 | 0.5 |
| aldehyde containing OF-Δxyl analogue | >4 | — | >8 |
| Undecylamine containing OF-Δxyl analogue | >4 | — | >8 |
| Dodecylamine containing OF-Δxyl analogue | >4 | — | >8 |
| DL-dihydrosphingosine containing OF-Δxyl analogue | 2 | 8 | >8 |

Example 3—Additional Examples OF-Δxyl Analogues

The aldehyde containing OF-Δxyl analogue can be used to create new analogues of occidiofungin besides the amine containing OF-Δxyl analogues described above. Synthesis of triazoles can be readily accomplished by addition of various aryl azide in the presence of Cu(ACAC) as a catalyst. This allows for the introduction of various aryl groups and conversion of the aldehyde into a triazole.

Synthesis of hydrazones: The aldehyde occidiofungin (1) can be treated with a variety of phenyl hydrazines such as i) 2-nitrophenyl hydrazine, 4-nitrophenyl hydrazine or 2,4-dinitrophenyl hydrazine (2,4 DNPH) to produce novel hydrazones. The nitro groups on these hydrazones can be readily reduced using a variety of reducing agents such as NaBH4/Pd, Pd/H2 and stannous chloride to produce the corresponding amines. The resulting aromatic amines can be subjected to reductive amination with a variety of aliphatic or aromatic aldehydes, such as acetaldehyde, linear chain aldehydes, branched chain alkyl aldehydes and benzaldehyde.

Example 4—Efficacy of OF-Δxyl Analogues for Treating VVC

Six to eight-week-old BALB/c mice would be intravaginally infected with C. albicans and dosed once per day with OF-Δxyl analogues for two to six days, particularly, three days. The OF-Δxyl analogue treated groups would be compared to a vehicle control group. Several groups of mice would be treated with various concentrations of OF-Δxyl analogues. The occidiofungin treated groups would be expected to reduce fungal load by more than two logs compared to control groups and significantly better than naturally occurring occidiofungins. The mice would be examined for outward signs of distress or irritation. No behavioral changes including sluggishness, stretching, or reluctance to consume food is expected. Furthermore, no vaginal bleeding or swelling is expected following OF-Δxyl analogue treatment.

The murine model of VVC has been reported by Yano et al. A variation of this method would be followed. Several groups of six mice would be used to evaluate several concentrations of OF-Δxyl analogue and vehicle control. Briefly, six to eight-week-old BALB/c mice would be treated subcutaneously with 200 ng per mouse of β-Estradiol 17-valerate three days prior to inoculation with *C. albicans* (D-3). A subcutaneous dose of estradiol would be administered every three days (D0, D3) until the end of the experiment to induce pseudo-estrus. Approximately a 20 μL intravaginal inoculation of a $2.5\times10^6$ colony forming units (CFU)/mL of *C. albicans* would define day zero (D0) of the VVC study. On the same day of inoculation (D0), another subcutaneous injection of estradiol would be made. OF-Δxyl analogues at several concentrations would be suspended in 20 μL of warm 0.3% Noble agar before intravaginal inoculation. Drug treatment would be done on day 2 (D2), day 3 (D3) and day 4 (D4) of the study. On day 5 (D5), the vaginal lumen would be lavaged with 100 μL of sterile PBS with a 200 μL pipette tip. Serial dilutions and total colony forming units per vaginal lavage would be determined by plating on YPD plates containing 50 μg/mL of chloramphenicol. The colony forming units (CFUs) obtained from each lavage would be counted on plates containing 30-300 colonies for determining the CFU/mL estimates. Body weight, signs of vaginal irritation such as swelling or bleeding and clinical signs of discomfort (stereotypical stretching behavior) would be monitored. Statistical analyses (T-test) would be done to compare the control group to treated groups and to compare differences between treated groups.

Example 5—Methods of Treating Fungal Infections

Intraperitoneal (ip) and subcutaneous routes of administration: Toxicological analysis of occidiofungin was carried out using a suspension of occidiofungin in solvents such as phosphate buffered saline (PBS), PBS containing 0.5% methylcellulose and 0.1% Tween 20. Occidiofungin was not completely soluble in these solvents and suspended particles were observed in the solution. Sonication mitigated the amount of suspended particles but not entirely. Occidiofungin was administered to female C57Bl/6 C3H F1 (B6C3F1) mice at age of 6 to 8 weeks via multiple routes and different doses to estimate toxicity.

Occidiofungin was administered by intraperitoneal injection in a single dose at 1, 5, 10, or 20 mg/kg in PBS of body weight. The compound was also administered in 1 dose at 10 mg/kg in sterilized 0.5% methylcellulose (constituted with 0.1% Tween-80 in PBS to promote solubility of test agent) by ip or subcutaneous injection. The excipient control in each experiment matched the vehicle. Control groups received sterile PBS or 0.5% methylcellulose with 0.1% Tween-80 in PBS. Body weight and clinical signs (movement, posture, skin lesions, appearance of fur indicating normal grooming, and behaviors) were recorded daily for 5 days. Necropsies were performed on study day 1 or study day 5 following the administration of occidiofungin. Blood and tissue samples were collected from animals dosed at 10 mg/kg with occidiofungin in 0.5% methylcellulose. One group of samples was collected on study day 1 following a single dose by ip injection. Another group was collected after 5-day observation with the same single dose through subcutaneous injection. Mice were anesthetized with isofluorane. Blood was then taken from the retroorbital plexus for serum biochemistry assays (alkaline phosphatase, alanine aminotransferase [ALT], aspartate aminotransferase [AST], gamma-glutamyl transferase, creatine kinase, blood urea nitrogen, creatinine) and hematology (white blood cell count and white blood cell differentiation). Body weight was measured immediately after mice were fully anesthetized and organs (spleen, thymus, brain, kidney, lung, and liver) were weighed and fixed in 10% neutral buffered formalin. Histological examination was performed on a portion of each organ by using routine paraffin-embedding technique and staining with hematoxylin and eosin (H & E).

Occidiofungin was also evaluated in a 5-day toxicity study by using 5 mice per group. Occidiofungin was dissolved in sterile PBS at dose of 2 mg/kg and administrated by ip injection daily for 5 consecutive days. The control group received sterile PBS. Body weight and clinical signs were recorded daily. Necropsies were performed on day 5 following the first administration of occidiofungin. Clinical chemistry, hematology (the same parameters as in the single-dose study), and histology (the same organs as in the single-dose study, except thymus) were evaluated. Histological sections were reviewed in the same manner as described above. Body weight, body weight change, organ weight, serum chemistry, and hematology data were analyzed by T test or 2-way analysis of variance (ANOVA) followed by Bonferroni posttest using Prism GraphPad software (San Diego, California). All the analyses were 2-sided, with $P<0.05$ considered statistically significant.

Results of intraperitoneal (ip) and subcutaneous routes of administration are as follows. The body weight differences ranged from 2% to 12% on the first day after treatment at various doses of occidiofungin in PBS (containing 0.5% methylcellulose or 0.2% Tween 20). At the end of the studies, it was clear that higher dose induced more body weight loss, and this change was dose responsive. However, this effect tended to diminish after the dosing ended, with a consequent regain of body weight during the following days. Daily dosing at 2 mg/kg for 5 days had a similar effect on day 5 as a single 5 mg/kg ip dose. Further, a decrease in absolute total white blood cell count in mice 1 day after ip administration of occidiofungin at 10 mg/kg was observed. There were no statistical differences in hematological or serum chemistry values 5 days after subcutaneous administration of occidiofungin at 10 mg/kg (Table 4).

TABLE 4

Hematology and serum chemistry in single dose experiments using occidiofungin in PBS.

| | Single Dose of Occidiofungin | |
|---|---|---|
| | 0 mg/kg | 10 mg/kg |
| | A: Hematology | |
| WBC (1000/μl) | 3.5 ± 0.3 | 1.9 ± 0.3 * |
| NEU (%) | 16.3 ± 2.8 | 11.6 ± 1.4 |
| LYM (%) | 77.5 ± 3.7 | 80.4 ± 2.2 |
| MONO (%) | 3.3 ± 0.7 | 6.8 ± 1.7 |

TABLE 4-continued Hematology and serum chemistry in single dose experiments using occidiofungin in PBS.

| | Single Dose of Occidiofungin | |
|---|---|---|
| | 0 mg/kg | 10 mg/kg |
| Serum Biochemistry | | |
| ALP (U/l) | 127.0 ± 2.0 | 67.0 ± 7.7 * |
| ALT (U/l) | 59.0 ± 5.6 | 58.0 ± 2.6 |
| AST (U/l) | 110.0 ± 13.3 | 160.0 ± 26.2 |
| GGT (U/l) | 20.0 ± 2.7 | 20.0 ± 1.6 |
| CK (U/l) | 146.3 ± 36.4 | 203.0 ± 31.6 |
| BUN (mg/dl) | 23.0 ± 1.2 | 21.0 ± 1.0 |
| CREAT (mg/dl) | 0.1 ± 0.1 | 0.1 ± 0.1 |

Effect of occidiofungin on hematology and serum chemistry. Animals were sacrificed the day after i.p. administration of occidiofungin. * Signifies statistically significant differences between treated and control group.

B:
Hematology

| WBC (1000/µl) | 4.1 ± 0.7 | 5.0 ± 1.4 |
|---|---|---|
| NEU (%) | 18.1 ± 2.6 | 30.8 ± 10.8 |
| LYM (%) | 73.8 ± 4.0 | 62.5 ± 12.7 |
| MONO (%) | 5.4 ± 2.5 | 4.6 ± 2.0 |
| Serum Biochemistry | | |
| ALP (U/L) | 81.5 ± 17.3 | 75.6 ± 11.7 |
| ALT (U/L) | 100.0 ± 44.6 | 20.4 ± 4.4 |
| AST (U/L) | 95.5 ± 37.1 | 69.4 ± 12.0 |
| GGT (U/L) | 8.0 ± 0.8 | 7.2 ± 2.3 |
| CK (U/l) | 154.0 ± 44.0 | 140.8 ± 30.4 |
| BUN (mg/dL) | 16.0 ± 0.8 | 13.6 ± 1.0 |
| CREAT (mg/dL) | 0.25 ± 0.05 | 0.20 ± 0.09 |

Effect of occidiofungin on hematology and serum chemistry. Animals were observed before sacrificing on day 5 after subcutaneous administration of occidiofungin.

In the repeat-dose study, white blood cell differential counts showed an increase in neutrophils and decrease in lymphocytes following a 5-day ip administration of occidiofungin at 2 mg/kg (Table 5).

TABLE 5

Hematology and serum chemistry in 5 day repeat dose experiment.

| | Single Dose of Occidiofungin | |
|---|---|---|
| | 0 mg/kg/day | 2 mg/kg/day |
| Hematology | | |
| WBC (K/ul) | 3.5 ± 1.0 | 5.6 ± 0.4 |
| NEU (%) | 18.0 ± 3.3 | 45.9 ± 1.9* |
| LYM (%) | 75.8 ± 3.9 | 46.4 ± 0.9* |
| MONO (%) | 3.6 ± 0.7 | 4.8 ± 1.1 |
| Serum Biochemistry | | |
| ALP (U/l) | 96.4 ± 9.5 | 39.6 ± 4.2* |
| ALT (U/l) | 49.8 ± 7.8 | 48.0 ± 6.5 |
| AST (U/l) | 104.0 ± 22.0 | 201.8 ± 59.6 |
| GGT (U/l) | 19.0 ± 6.0 | 15.2 ± 2.9 |
| CK (U/l) | 401.8 ± 123.9 | 401.0 ± 114.4 |
| BUN (mg/dl) | 24.4 ± 4.3 | 18.0 ± 2.8 |
| CREAT (mg/dl) | 0.38 ± 0.07 | 0.18 ± 0.09 |

Effect of occidiofungin on hematology and serum chemistry. Animals were observed before sacrificing on day 5 after i.p. administration of occidiofungin.
*Signifies statistically significant differences between treated and control group.

Although there were some statistically significant differences in serum clinical chemistry parameters, no consistent dose-response effects were noted, which suggests that the significant effects represented normal biological variation or experimental effects are not directly related to the action of the test compound. Generally, no macroscopic findings were observed by histological examination. No observable differences were present in the microscopic cell morphology or macroscopic tissue morphology of brain, liver, lung, thymus, or kidney. One finding was a decrease in activated thymocytes in the medulla in the 10 mg/kg single-dose toxicity study. This result in conjunction with decreased thymus weight or increased neutrophil percentages suggests that occidiofungin causes a nonspecific stress response. Another likely explanation is that there is an allergic response to the presence of the xylose on occidiofungin causing an increase in neutrophils. In summary, there was no clear evidence for organ-specific histological effects of occidiofungin.

Intravenous (iv) administration of occidiofungin Six to eight-week-old female BALB/c mice (5 mice per group) were given occidiofungin dissolved in 1.5% hydroxy propyl-beta-cylcodextrin suspended in phosphate buffered saline (PBS). Spectrometric inspection at O.D.600 following addition of vehicle to the purified dried drug had negligible absorbance difference to vehicle without drug, suggesting that the drug went into solution. For the experiments, occidiofungin was administered by intravenous (i.v.) injection into the tail vein at a single dose at 5 mg/kg of body weight. The excipient control in each experiment matched the vehicle. Body weight and clinical signs (movement, posture, skin lesions, appearance of fur indicating normal grooming, and behaviors) were recorded following administration at one, four, eight, sixteen, and twenty-four hours. Necropsies were performed at 24 hours following administration of occidiofungin. Blood and tissue samples from animals dosed at 5 mg/kg of body weight with occidiofungin in 1.5% hydroxy propyl-beta-cylcodextrin suspended in PBS were taken 24 hours following excipient or drug administration. Mice were anesthetized with isofluorane. Blood was then taken from the retroorbital plexus or heart puncture for serum biochemistry assays (alkaline phosphatase, alanine aminotransferase, aspartate aminotransferase, albumin, and blood urea nitrogen) and hematology (white blood cell count and white blood cell differentiation). Body weight was measured immediately before treatment and 24 hours later before the mice were fully anesthetized and fixed in 10% neutral buffered formalin. Histological examination was performed on a portion of each organ by using routine paraffin embedding technique and staining with hematoxylin and eosin (H & E).

Results of intravenous (iv) administration of occidiofungin are as follows. Following administration of occidiofungin intravenously, mice weight ranged between 0% to 21% body weight-loss 24 hours after treatment and had an average weight loss of 6.2%. Excipient treated mice body weight showed 8% to 13% body weight gain 24 hours after treatment and had a 9.6% average increase in body weight. A consistent behavioral response was observed at 1 hour and to a lesser extent at 4 hours post i.v. administration, in which the mice were more lethargic than excipient treated mice and had ruffled fur. They were responsive to touch but would move slower than excipient treated mice. Treatment was not associated with more typical rodent behaviors associated with severe pain (e.g., writhing, vocalization, or lack of spontaneous locomotion). No other behavioral signs were observed. Mice behavior appeared to be normal by 8, 16, and 24 hour post injection. Generally, no macroscopic findings were observed by histological examination performed on tissues removed from the euthanized mice at 48 hours post injection. No observable differences were present in the microscopic cell morphology or macroscopic tissue morphology of esophagus, stomach, small intestine, colon, liver, pancreas, spleen, kidneys, lungs, heart and brain. Albumin and blood urea nitrogen (BUN) tests were similar for occidiofungin treated and excipient treated mice (Table 6). These blood tests are indicative of normal kidney and liver function. In addition, alkaline phosphatase (ALP) tests were similar between drug and excipient treated mice (Table 6). These results indicate normal liver and bone cell function. Normally aspartate amino transferase (AST) and alanine aminotransferase (ALT) tests are performed in combination with ALP to assess liver function. Elevated levels of AST and ALT do suggest heart or liver damage, but do not necessarily indicate severe organ damage. Generally, a ratio of AST to ALT less than one is indicative of liver damage. The ratio in all treated mice was greater than one, suggesting that the liver is not damaged. AST values ranged from 177 to 1528 (U/l) with a mean value of 765 (U/l) and the ALT values ranged from 144 to 1273 (U/l) with a mean value of 521 (U/l) (Table 6). Given the variability in AST and ALT levels in treated mice, only the ALT levels were statistically significant. White blood cell (WBC) counts were not statistically different between treated and untreated mice. This suggests that occidiofungin i.v. administration at 5 mg/kg had no cytotoxicological effect on blood cells or bone marrow. The absence of elevated levels further suggests normal spleen function. The percentage of neutrophils was statistically different in drug and excipient treated mice, while the percentages of lymphocytes was not statistically different (Table 6).

TABLE 6

Percent body weight change, serum chemistry and hematology following intravenous administration of drug and excipient control.

| | Single IV Dose of Occidiofungin | |
|---|---|---|
| | 5 mg/kg | 0 mg/kg |
| *Weight Change % | −6.2 ± 9.9 | +9.6 ± 1.9 |
| Serum Biochemistry | | |
| Albumin (g/dl) | 3.1 ± 0.6 | 3.6 ± 0.2 |
| BUN (mg/dl) | 29.6 ± 5 | 24.5 ± 3.3 |
| ALP (U/l) | 99 ± 34 | 116 ± 17 |
| AST (SGOT) U/l | 765 ± 692 | 165 ± 81 |
| *ALT (SGPT) U/l | 521 ± 652 | 36 ± 10 |
| Hematology | | |
| WBC estimate | 4750 ± 1225 | 5830 ± 1550 |
| *Neutrophils % | 43 ± 14 | 16 ± 5 |
| Lymphocytes % | 54 ± 15 | 83 ± 7 |
| Platelet estimate (xK/ul) | 39 ± 21 | 58 ± 58 |

Animals were sacrificed 24 hours following i.v. administration of occidiofungin.
*Signifies statistically significant differences between treated and control group. $p < 0.05$ was considered statistically significant.

The increase in neutrophils is likely attributed to an allergic response due to the presence of the xylose on occidiofungin. There was no statistical difference in platelet counts between drug and excipient treated mice, suggesting that occidiofungin does not affect platelet production by the bone marrow or destroy circulating platelets. The increase in neutrophils was not observed in mice treated with OF-Δxyl (Table 7). In summary, there was no evidence for organ specific histological effects of occidiofungin. There were no apparent undesirable effects observed in the serum clinical chemistry and hematology parameters that would preclude additional animal testing of the compound. However, the increase in neutrophils does suggest a possible allergic response that appears to be alleviated with the removal of xylose.

TABLE 7

Hematology following intravenous administration of occidiofungin and OF-Δxyl drug.

| | Single IV Dose of Occidiofungin or OF-Δxyl (5 mg/kg) | |
|---|---|---|
| Hematology | | |
| *Neutrophils % | 26 ± 8.4 | 5 ± 0.7 |
| Lymphocytes % | 72 ± 9.2 | 95 ± 0.7 |

Treatment of Vulvovaginal Candidiasis

Current antifungal treatment options are plagued with rapidly increasing occurrence of resistance, high degree of toxicity and a limited spectrum of activity. Novel antifungal agents with a unique target, wider spectrum of activity, and reduced toxicity to the host are desired. This example characterizes occidiofungin produced by *Burkholderia contaminans* MS14. The cellular target of the occidiofungin was determined to be actin. Actin binding metabolites are generally characterized by their ability to inhibit polymerization or depolymerization of actin filaments, which presumably accounts for their severe toxicity. Occidiofungin, instead, has a subtler effect on actin dynamics that triggers apoptotic cell death. The efficacy of the antifungal is demonstrated in treating a vulvovaginal yeast infection in a murine model.

Occidiofungin has a wide spectrum of activity against filamentous and non-filamentous fungi and minimal toxicity in an animal system. The mechanism of action of occidiofungin differs from the primary mode of action of the three common classes of antifungals. Occidiofungin has been observed to rapidly induce apoptosis in yeast cells at the minimal inhibitory concentrations. The primary cellular target of occidiofungin is actin. Actin-mediated cellular processes in yeast, such as endocytosis, nuclear segregation and hyphal formation, were all disrupted following addition of subinhibitory concentrations of occidiofungin. Occidiofungin's binding to actin interferes with F-actin filament cable stability and does not interfere with polymerization or depolymerization of actin filaments. Occidiofungin binds to F-actin with an estimated dissociation constant (Kd) of 1000 nM and has a high saturation of binding ratio of more than twenty molecules of occidiofungin to one actin monomer. Given the high binding ratio, it was predicted that the microscopic Kd value (which captures the affinity of one occidiofungin molecule binding to actin) is significantly lower than the 1000 nM dissociation constant.

In the repeat-dose toxicity study, the hematology tests revealed that white blood cell differential counts showed an increase in neutrophils and decrease in lymphocytes. Neutrophils play important roles in host defense against all classes of infectious agents and pathology of various inflammatory conditions. The increase in neutrophils also suggests a possible inflammatory or mild stress response. A potential reason for the observed response is the presence of a xylose moiety on the novel amino acid 2 (NAA2) or the NAA2 residue itself (FIG. 1). Mammalian immune system can recognize N-glycans containing β-(1,2)-xylose and α-(1,3)-fucose residues. Novel analogs at the NAA2 position of occidiofungin were synthesized to test whether the xylose on NAA2 residue is responsible for the development inflammation response.

In addition, occidiofungin has sub-micromolar activity against *Pythium* species which lacks ergosterol in the membrane and against *Cryptococcus neoformans* which is resistant to echinocandins. Preliminary toxicological analyses of occidiofungin using a murine model indicated that it was well tolerated at concentrations of 10 to 20 mg/kg, but it demonstrates a mild allergic or stress response. Blood chemistry analyses and histopathology performed on multiple organs showed a transient non-specific stress response with no damage to organ tissues. These data suggest that occidiofungin is a promising candidate for development as a clinically useful antifungal agent.

Spectrum of activity of occidiofungin against clinically relevant fungi Occidiofungin causes cell death in fungi through a mechanism of action that is distinct from the clinically used classes of antifungals. Due to its unique mechanism of action, occidiofungin has sub-micromolar activity against azole and echinocandin resistant strains of fungi. Strains of *Candida albicans, Candida glabrata*, and *Candida parapsilosis* that were resistant to fluconazole and caspofungin were sensitive to occidiofungin (Table 8). Non-albicans strains are believed to be the primary cause of recurrent vulvovaginal candidiasis. Furthermore, strains of *Candida parapsilosis* and *C. neoformans* that were resistant to treatment with caspofungin were found to be susceptible to treatment with occidiofungin. Occidiofungin was also found to have a broader spectrum of activity than clinically available antifungals and was found to be active against *Aspergillus, Mucor, Fusarium*, and *Rhizopus* species. Several strains of the dermatophyte *Trichophyton* were found to also be susceptible to occidiofungin treatment, including azole and terbinafine resistant strains. A summary of the results, as reported in Table 8, indicate that occidiofungin has activity against filamentous and non-filamentous fungi at sub-micromolar concentrations and has a broader spectrum of activity compared to other clinically available antifungals. Furthermore, sensitivity of fungal strains resistant to azoles and echinocandin class of antifungals, support the notion that occidiofungin is functioning via a novel mechanism of action.

Occidiofungin has sub-micromolar activity against azole and echinocandin resistant strains of fungi. Susceptibility of multiple strains of each species (Filamentous fungi: *Aspergillus fumigatus, Aspergillus flavus, Fusarium* sp. (including *solani* and *oxysporum*), *Mucor* sp., *Rhizopus* sp., *Trichophyton rubrum*, and *Trichophyton mentagrophytes*; and Yeasts: *C. albicans, C. glabrata, C. krusei, C. parapsilosis, C. tropicalis*, and *Cryptococcus neoformans*) to occidiofungin was tested and antibiotic resistant strains were used when available (Table 8). Fluconazole resistant *C. albicans* and *C. glabrata* were sensitive to occidiofungin. Inhibitory concentrations of occidiofungin to these isolates were ≤2 µg/mL, while the MIC of fluconazole against these strains was ≥32 µg/mL. *Rhizopus* spp. and *C. neoformans* were more sensitive to occidiofungin than fluconazole. *Cryptococcus neoformans* is insensitive to echinocandins, but is susceptible to occidiofungin at sub-micromolar concentrations.

Minimum inhibitory concentration (MIC) susceptibility testing was performed according to the CLSI M27-A3 and M38-A2 standards for the susceptibility testing of yeasts and filamentous fungi, respectively. Incubation temperature was at 35° C. and the inoculum size was $0.5-2.5 \times 10^3$ colony-forming units (CFU)/mL and $0.4-5 \times 10^4$ conidia/mL for yeasts and filamentous fungi, respectively. Inoculum concentration for dermatophytes was $1-3 \times 10^3$ conidia/mL. RPMI was used throughout as the growth medium and *Cryptococcus* strains were tested in YNB. Occidiofungin MICs were recorded at 50% and 100% growth inhibition after 24 and 48 hours of incubation, with the exception of dermatophytes which were incubated for 96 hours. Fluconazole MICs against *Candida* strains were recorded at 50% inhibition after 24 hours and against *Cryptococcus* strains after 72 hours. Voriconazole MICs were recorded at 100% inhibition after 24 hours for zygomycetes and after 48 hours for *Fusarium* and *Aspergillus* strains. Voriconazole MICs were recorded at 80% inhibition after 96 hours of incubation for dermatophytes. *S. cerevisiae* deletion mutants were obtained from the commercially available BY4741 deletion library (Thermo Scientific). Susceptibility testing was carried out on inoculum size of $0.5-1 \times 10^4$ cells/ml in YPD media at 30° C. and MICs recorded after 48 and 60 hours.

Development of Occidiofungin as a Treatment for VVC

The work that is being conducted will lead to a new, first-in-class anti-infective chemotherapeutic targeted specifically for fungal infections. Fungal pathogens infect more than 7,000,000 adults in the US each year and are a significant source of economic health cost for society. The lead molecule occidiofungin serves as a platform for development of t therapies to treat VVC.

In the United States it is estimated that seventy percent of the female population will suffer from VVC. A subset of this population, nearly 5,000,000 women annually, suffer from RVVC. RVVC's estimated health care cost in the USA is $4-5 billion per year. This estimate is based on increased medical costs to treat VVC and the economic impact from lost productivity. The global cost of VVC and RVVC is expected to be over 10 billion per year. VVC and RVVC also place a significant cost on quality of life for any infected individual, their family, and employers. Although there are several preventative measures in development, there is no effective therapeutic. An effective therapeutic that could treat VVC in a relatively non-invasive methodology could significantly reduce the cost to patients, while at the same time increase their quality of life. Overall, a new therapeutic would reduce the impact of these infections on the economy. Additionally, there is a growing concern over the increase in drug resistant strains of *Candida* and the lack of new treatment of options available. These resistant strains are expected to increase the global costs associated with RVVC.

Occidiofungin is superior in clinical setting as an antifungal for several reasons. For example, its antifungal activity has been demonstrated against a wide array of fungi, including those resistant to current antifungals in use. MICs of occidiofungin against *Candida* species are between 0.5 and 2.0 µg/mL, which is similar in activity to echinocandins and amphotericin B. Pharmacodynamic (Time Kill) experiments revealed that occidiofungin is rapidly fungicidal against *Candida albicans*, which is better than current clinically approved antifungals. Occidiofungin retains its in vitro potency in the presence of 5% and 50% human serum with a minimum lethal concentration (MLC) of 2 and 4 µg/mL, respectively. An alternative target for occidiofungin other than targeting ergosterol production, binding to ergosterol, or inhibiting the 1,3-β-glucan synthase enzyme, is advantageous because these mechanisms are prone to resistance. In vivo toxicity studies show that body and organ weight changes induced by occidiofungin are not associated with any negative gross or microscopic findings. Hematology and serum biochemistry tests reveal that occidiofungin does not significantly alter functions of organs. Occidiofungin demonstrates a significant reduction in fungal load in murine VVC and system yeast infection models.

These factors provide occidiofungin with unique advantages that are necessary to be an effective treatment for VVC and RVVC.

Efficacy of Occidiofungin in Treating a Murine Model of VVC

Figure 7:
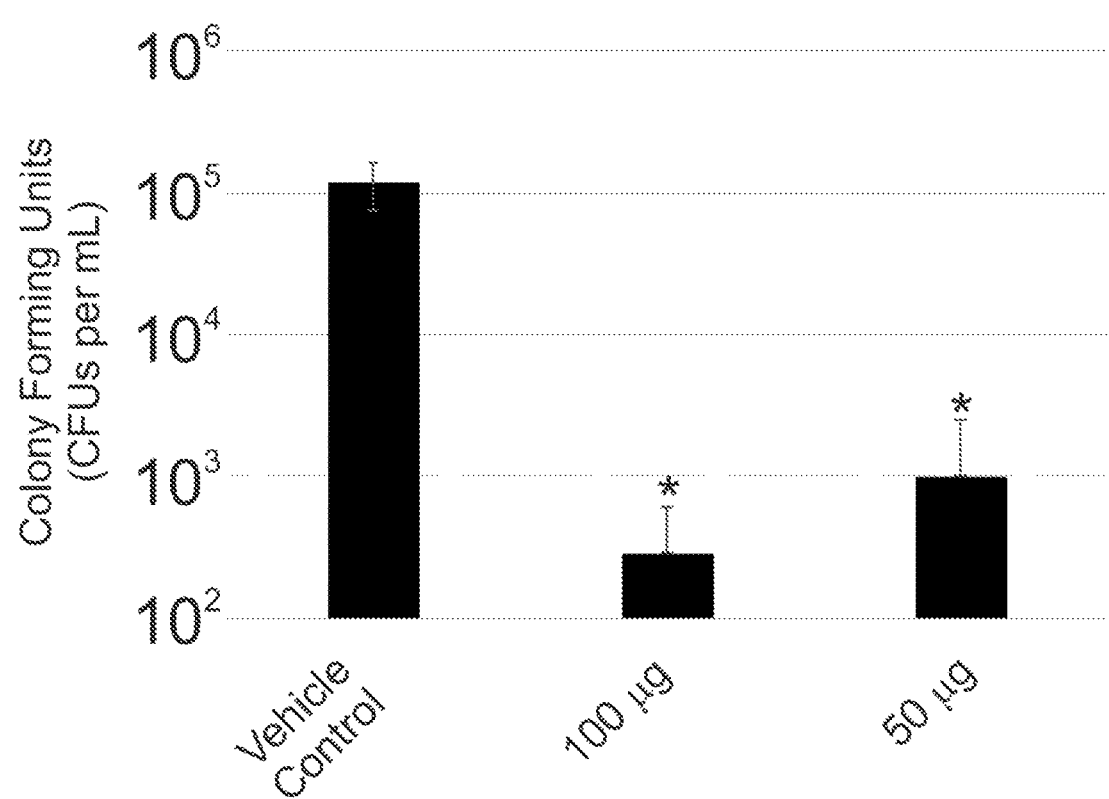
FIG. 7. Efficacy of occidiofungin in treating murine vulvovaginal candidiasis. The graph demonstrates CFUs per ml of Candida albicans in the control group of mice compared to the groups treated intravaginally with different concentrations of occidiofungin in 0.3% noble agar. Error bars represent standard deviation. Statistical analyses indicate a significant difference between the control group and the treated groups (p<0.001) as indicated by the asterisk.

Six to eight-week-old BALB/c mice were intravaginally infected with *C. albicans* and dosed once per day with occidiofungin for three days. The occidiofungin treated groups were compared to a vehicle control group. Three groups of six mice were treated with 100, 50, and 0 µg of occidiofungin suspended in 0.3% Noble agar. The occidiofungin treated groups reduced fungal load by more than two logs (FIG. 7). The reduction in fungal load with both treatment groups was statistically significant from vehicle control (p<0.001). There was no statistically significant difference between the treated groups (p=0.33), suggesting that the lower limit of occidiofungin dosing was not achieved in the experiment. During the course of the study, the mice were examined for outward signs of distress or irritation. No behavioral changes including sluggishness, stretching, or reluctance to consume food was observed. Furthermore, no vaginal bleeding or swelling was observed following treatment.

The murine model of VVC has been reported by Yano et al. A variation of this method was followed. Three groups of six mice were used to evaluate two concentrations of occidiofungin (100 µg and 50 µg) and vehicle control (0.3% Noble agar). Briefly, six to eight-week-old BALB/c mice were treated subcutaneously with 200 ng per mouse of β-Estradiol 17-valerate three days prior to inoculation with *C. albicans* (D-3). A subcutaneous dose of estradiol was administered every three days (D0, D3) until the end of the experiment to induce pseudo-estrus. Approximately a 20 µL intravaginal inoculation of a 2.5×10$^6$ colony forming units (CFU)/mL of *C. albicans* defines day zero (D0) of the VVC study. On the same day of inoculation (D0), another subcutaneous injection of estradiol was made. Lyophilized powder of occidiofungin containing either 100 µg or 50 µg of occidiofungin was suspended in 20 µL of warm 0.3% Noble agar before intravaginal inoculation. Drug treatment was done on day 2 (D2), day 3 (D3) and day 4 (D4) of the study. On day 5 (D5), the vaginal lumen was lavaged with 100 µL of sterile PBS with a 200 µL pipette tip. Serial dilutions and total colony forming units per vaginal lavage were determined by plating on YPD plates containing 50 µg/mL of chloramphenicol. The colony forming units (CFUs) obtained from each lavage were counted on plates containing 30-300 colonies for determining the CFU/mL estimates. Body weight, signs of vaginal irritation such as swelling or bleeding and clinical signs of discomfort (stereotypical stretching behavior) were monitored. Statistical analyses (T-test) were done to compare the control group to treated groups and to compare differences between treated groups. All the analyses were 2-sided, with P<0.05 considered statistically significant.

TABLE 8

Activity of occidiofungin against filamentous and non-filamentous fungi.

| Species | Occidiofungin (µg/mL) | | | | | | | | Voriconazole MIC (µg/mL) | Fluconazole MIC (µg/mL) |
| | 24 hours | | 48 hours | | 72 hours | | 96 hours | | | |
| | 50% | 100% | 50% | 100% | 50% | 100% | 80% | 100% | | |
| *Trichophyton mentagrophytes 10207 | | | | | | | 1 | 2 | 0.25 | >16 |
| Trichophyton mentagrophytes 28556 | | | | | | | 1 | 2 | 0.06 | >16 |
| Trichophyton mentagrophytes 28641 | | | | | | | 1 | 2 | 0.06 | 16 |
| &Trichophyton rubrum 11199 | | | | | | | 1 | 2 | 0.008 | 0.25 |
| Trichophyton rubrum 28658 | | | | | | | 1 | 2 | 0.03 | 2 |
| Trichophyton rubrum 28659 | | | | | | | 1 | 2 | 0.03 | 2 |
| Rhizopus microsporus 28506 | 4 | 8 | — | 8 | | | | | 16 | |
| Rhizopus oryzae 28403 | 4 | 8 | — | 8 | | | | | >16 | |
| Rhizopus microsporus 27785 | 2 | 4 | — | 8 | | | | | >16 | |
| Mucor circinelloides 19445 | 4 | 8 | 4 | 8 | | | | | >16 | |
| Mucor racemosus 27784 | 2 | 4 | — | 4 | | | | | >16 | |
| Mucor fragdis 27782 | 2 | 4 | — | 4 | | | | | >16 | |

TABLE 8-continued

Activity of occidiofungin against filamentous and non-filamentous fungi.

| | Occidiofungin (µg/mL) | | | | | | | | Voriconazole MIC (µg/mL) | Fluconazole MIC (µg/mL) |
|---|---|---|---|---|---|---|---|---|---|---|
| | 24 hours | | 48 hours | | 72 hours | | 96 hours | | | |
| Species | 50% | 100% | 50% | 100% | 50% | 100% | 80% | 100% | | |
| *Fusarium solani* 28386 | 2 | 4 | — | 4 | | | | | >16 | |
| *Fusarium oxysporum* 27718 | 2 | 4 | — | 4 | | | | | >16 | |
| *Fusarium solani* 18749 | 2 | 4 | 2 | 4 | | | | | >16 | |
| *Aspergillus flavus* 28517 | — | 4 | — | 4 | | | | | 1 | |
| *Aspergillus flavus* 28455 | 2 | 4 | — | 4 | | | | | 2 | |
| *Aspergillus flavus* 28445 | 2 | 4 | — | 4 | | | | | 2 | |
| *Aspergillus fumigatus* 28434 | — | 4 | — | 4 | | | | | 1 | |
| *Aspergillus fumigatus* 28435 | — | 2 | — | 2 | | | | | 1 | |
| *Aspergillus fumigatus* 28436 | 2 | 4 | 2 | 4 | | | | | 1 | |
| #*Candida albicans* 23512 | — | 1 | — | 2 | | | | | | 32 |
| *Candida albicans* 28200 | 4 | 8 | 4 | 8 | | | | | | 8 |
| *Candida albicans* 28102 | — | 2 | — | 2 | | | | | | 0.125 |
| #*Candida glabrata* 27243 | 2 | 4 | — | 4 | | | | | | 64 |
| *Candida glabrata* 25742 | — | 2 | — | 2 | | | | | | 4 |
| *Candida glabrata* 28271 | 4 | 8 | 4 | 8 | | | | | | >64 |
| *Candida krusei* 9541 | 2 | 4 | — | 4 | | | | | | 16 |
| #*Candida krusei* 28415 | 4 | 8 | 4 | 8 | | | | | | 64 |
| *Candida krusei* 28570 | 4 | 8 | 4 | 8 | | | | | | 16 |
| +*Candida parapsilosis* 2006 | 2 | 4 | — | 4 | | | | | | 0.125 |
| *Candida parapsilosis* 28364 | 4 | 8 | 4 | 8 | | | | | | 0.25 |
| *Candida parapsilosis* 28174 | — | 4 | — | 4 | | | | | | 0.25 |
| *Candida tropicalis* 9624 | — | 2 | — | 2 | | | | | | 0.25 |

TABLE 8-continued

Activity of occidiofungin against filamentous and non-filamentous fungi.

| | Occidiofungin (µg/mL) | | | | | | | | Voriconazole MIC (µg/mL) | Fluconazole MIC (µg/mL) |
|---|---|---|---|---|---|---|---|---|---|---|
| | 24 hours | | 48 hours | | 72 hours | | 96 hours | | | |
| Species | 50% | 100% | 50% | 100% | 50% | 100% | 80% | 100% | | |
| Candida tropicalis 28272 | 4 | 8 | 4 | 8 | | | | | | 0.125 |
| Candida tropicalis 28478 | 4 | 8 | 4 | 8 | | | | | | 0.125 |
| +Cryptococcus neoformans 19526 | | | | | — | 2 | | | | 4 |
| Cryptococcus neoformans 27708 | | | | | — | 2 | | | | 2 |
| Cryptococcus neoformans 28446 | | | | | — | 1 | | | | 4 |

Example 6—Actin Binding Properties of Occidiofungin Analogs

Figure 9A:
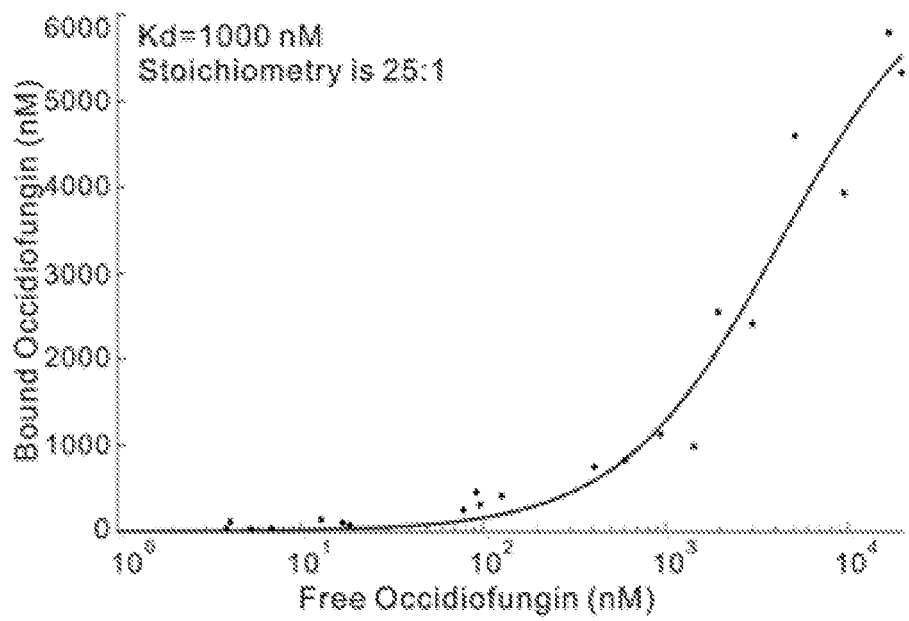
FIGS. 9A-9D. Co-sedimentation assay demonstrating the binding of occidiofungin analogs to actin. (A) Binding curve of native occidiofungin to actin (Kd=1000 nM; the stoichiometry [ligand:protein] is 25: 1. (B) Binding curve of the dodecylamine analog to actin (Kd=4200 nM; the stoichiometry [ligand:protein] is 34: 1. (C) Binding curve of phalloidin to actin (Kd=8 nM; the stoichiometry [ligand:protein] is 0.7:1. (D) Binding curve of the dihydrosphingosine analog to actin (Kd=25 nM; the stoichiometry [ligand:protein] is 1.8:1. The graph is plotted between the amount of free compound obtained in the supernatant of the co-sedimentation assay and the amount of bound compound obtained from the actin pellet. Data for native occidiofungin and phalloidin has been published previously (Ravichandran et al.).
Figure 9B:
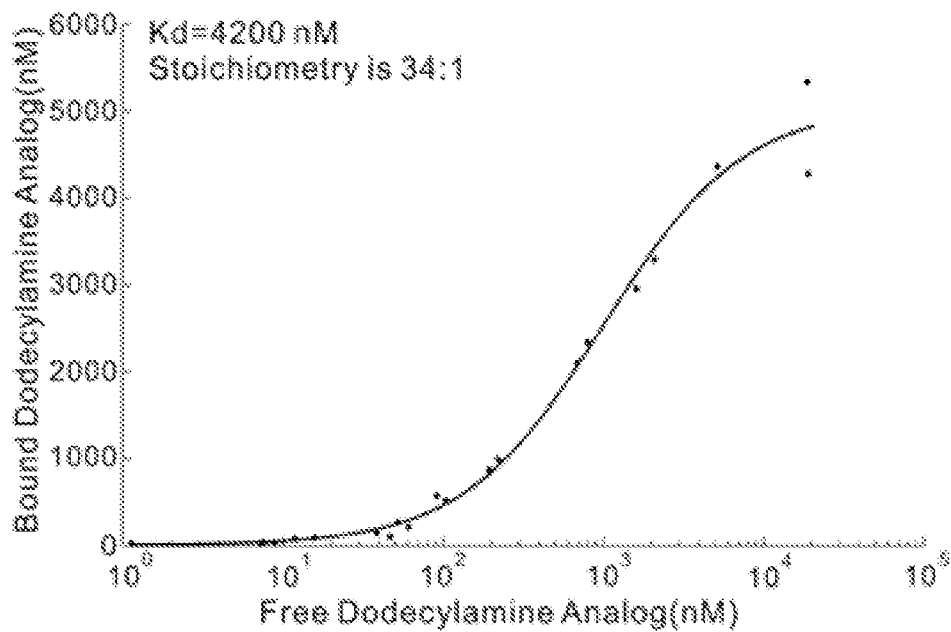
Figure 9C:
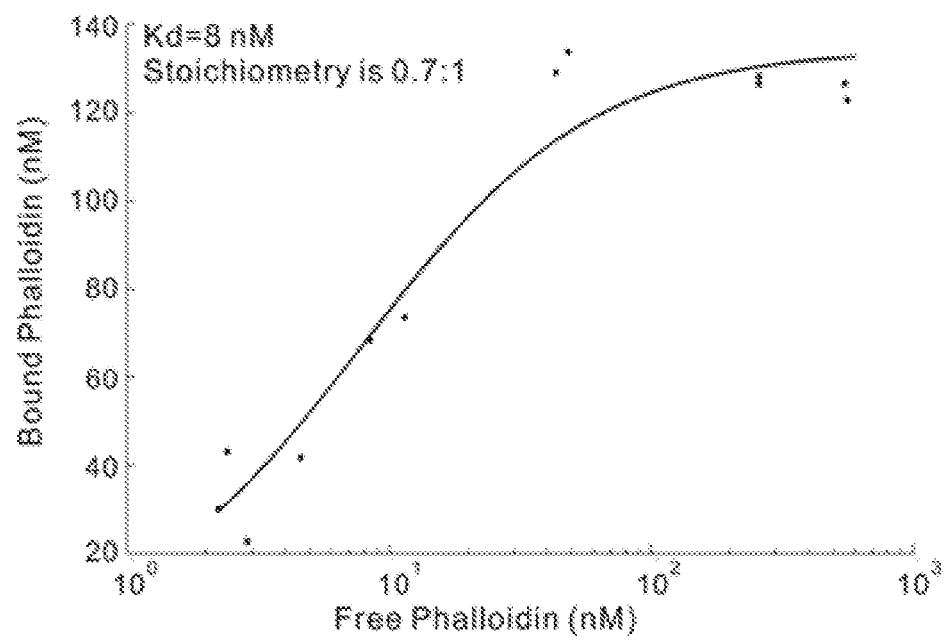
Figure 9D:
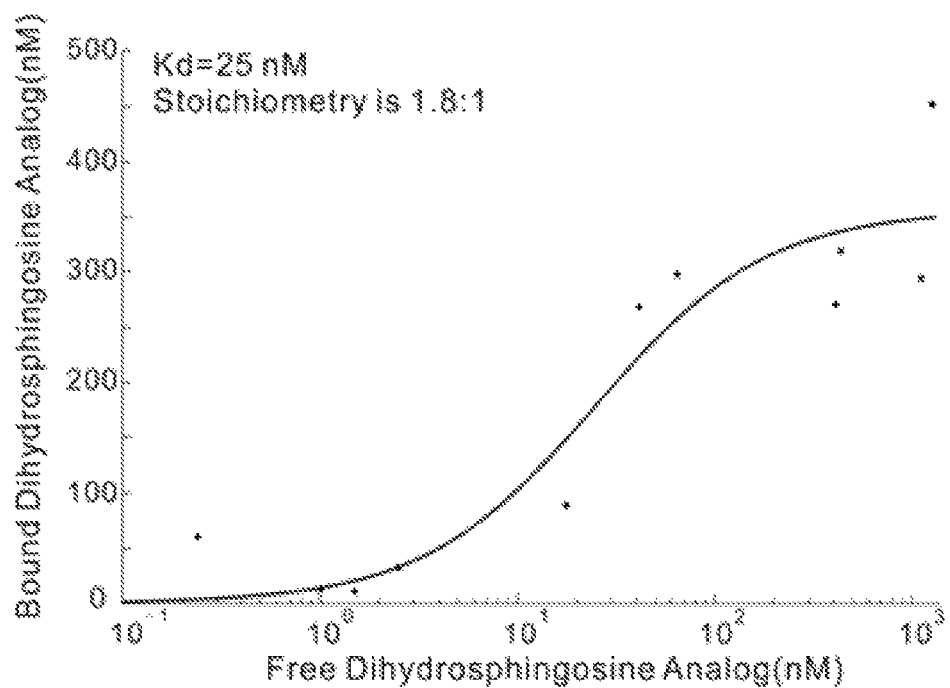

To characterize the actin binding properties of the dodecylamine and dihydrosphingosine analogs of occidiofungin, a co-sedimentation assay was performed. Native occidiofungin had a Kd value of 1000 nM and a saturation of binding ratio of ~25:1 (ligand:actin monomer, FIG. 9A). Further, phalloidin had an estimated Kd value of ~8 nM with a saturation of binding ratio of ~0.7:1 (ligand:actin monomer, FIG. 9C). The dodecylamine analog was determined to have a Kd value of 4200 nM with a saturation of binding ratio of ~34:1 (ligand:actin monomer) (FIG. 9B). Interestingly, the dihydrosphingosine analog had a Kd value of 25 nM with a saturation of binding ratio of ~1.8:1 (ligand:actin monomer, FIG. 9D). The dodecylamine analog had a similar saturation of binding to actin as the native compound with approximately a 4-fold lower binding affinity to actin. The dihydrosphingosine analog showed an actin binding property closer to phalloidin's and had a 13.5-fold lower saturation of binding ratio than native occidiofungin. The decrease in dissociation constant is likely attributed to the low saturation of binding for the dihydrosphingosine analog compared to native occidiofungin and not an increase in affinity to actin.

Figure 10A:
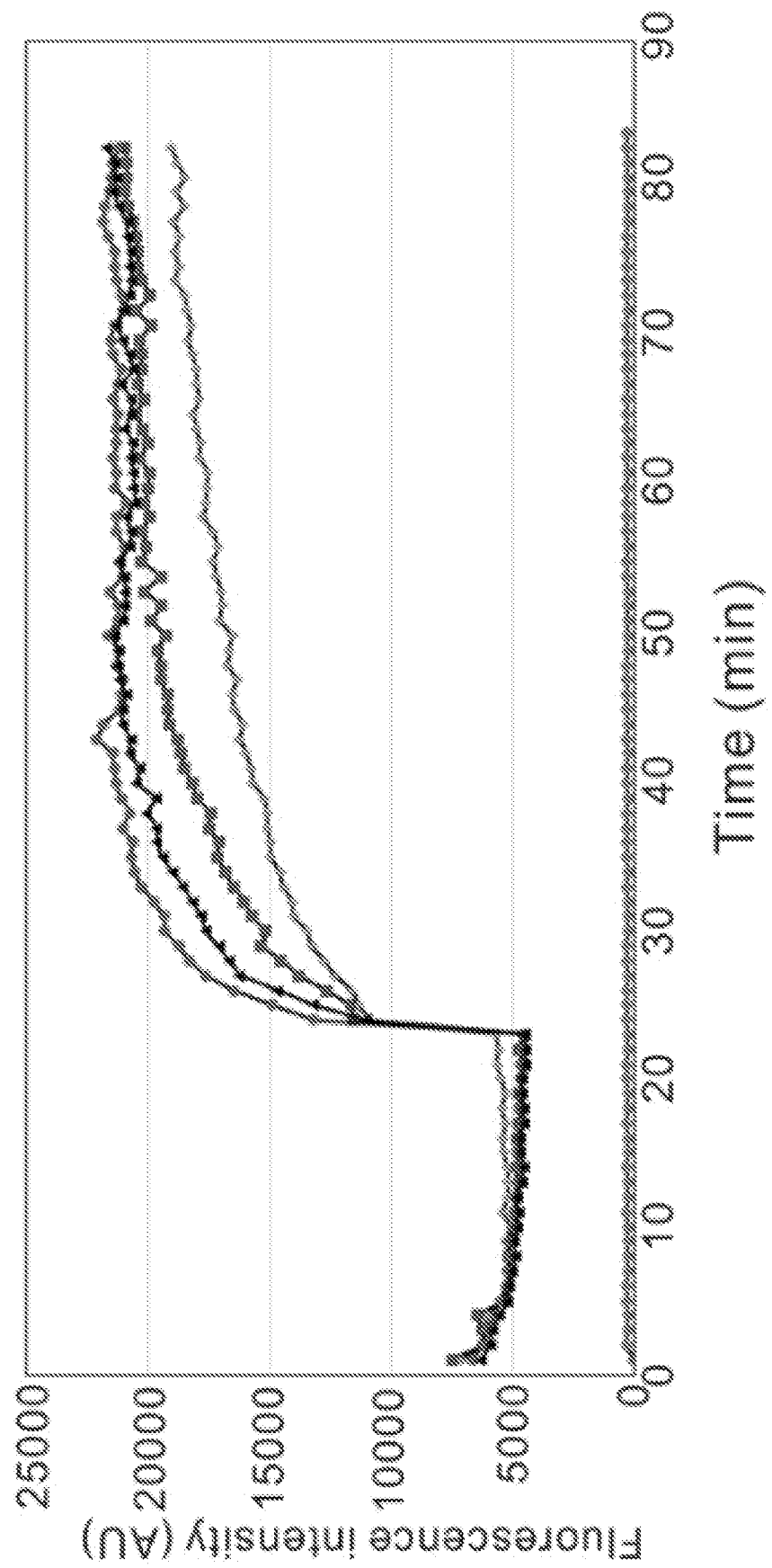
FIGS. 10A-10B. Pyrene labeled actin polymerization and depolymerization assay. The effect of phalloidin, native occidiofungin, and the dihydrosphingosine analog on actin (A) polymerization and (B) depolymerization assays. (grey •) represents buffer baseline control; (■) represents no drug control; (♦) represents phalloidin treatment; (black •) represents native occidiofungin treatment; (▲) represents dihydrosphingosine analog treatment. The fluorescent data is measured in terms of arbitrary units (AU).
Figure 10B:
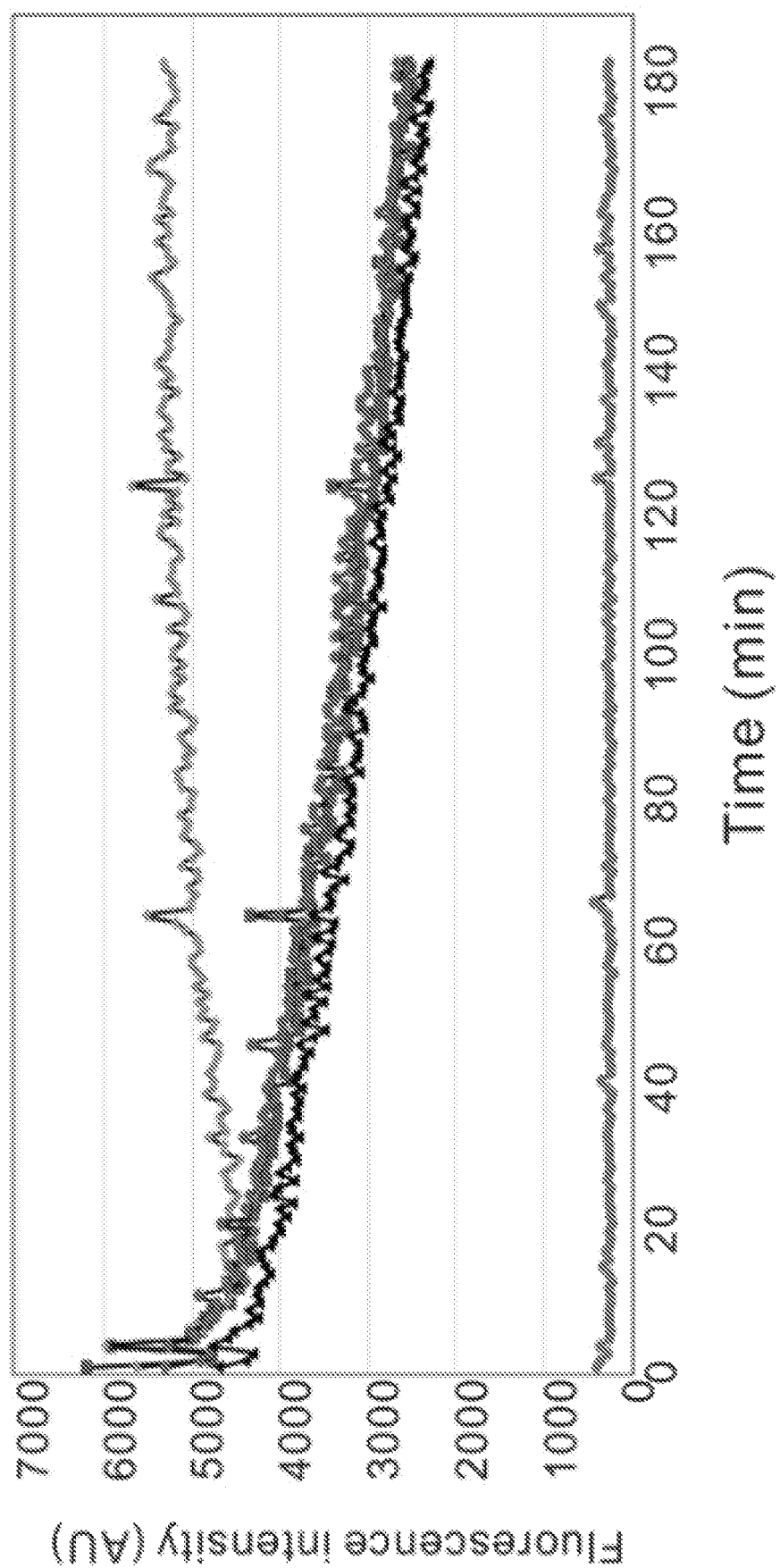

Given that the actin binding properties of the dihydrosphingosine analog were different from native occidiofungin, the analog was tested to determine whether its mechanism of actin binding was different than native occidiofungin. Native occidiofungin does not interfere with actin polymerization or depolymerization, but rather interferes with actin cable formation triggering ROS accumulation and apoptotic cell death. The molar ratio of occidiofungin, analogs of occidiofungin, or phalloidin to actin in the polymerization and depolymerization assay was close to 1:1. The pyrene fluorescence readings approximately one hour after incubation in the polymerization buffer plateaued at around 19,000 for phalloidin and 21,000 AU for the dihydrosphingosine analog and native occidiofungin (FIG. 10). Following incubation in the depolymerization buffer, actin filaments incubated with phalloidin had pyrene fluorescent readings above 5,000 AU, while actin filaments incubated with dihydrosphingosine analog and native occidiofungin had similar readings as no drug control at 2,500 AU. Phalloidin completely blocked the depolymerization of F-actin. The dihydrosphingosine analog did not interfere with polymerization or depolymerization of actin, similar to what was observed with native compound (FIG. 10). The lack of any interference with the polymerization or depolymerization of actin by the dihydrosphingosine analog supports the assumption that the dihydrosphingosine analog and native occidiofungin have the same binding region on actin.

Example 7—Improved Analogs of Occidiofungin

This example provides strategies to produce novel analogs of occidiofungin. Oxidative cleavage of the diol group present in the aliphatic chain of NAA2 followed by reductive aminations of alkyl amines restored the aliphatic structure of the native compound. The methods described to synthesize the analogs of occidiofungin provide an efficient strategy for generating novel analogs of occidiofungin. One of the analogs synthesized was identified to have reduced antifungal activity but significantly lower dissociation constant and stoichiometry in an actin co-sedimentation study. These results showed that the fatty acid moiety in native occidiofungin plays an important role with regards to its antifungal activity and actin binding properties.

Occidiofungin needs to enter the cell to reach its cellular target actin. Against S. cerevisiae, the undecylamine and dodecylamine analogs were both inactive at a concentration that was sixty-four-fold higher than native compound, while the dodecylamine analog only had a four-fold reduction in affinity for actin. The lack of activity of undecylamine and dodecylamine analogs suggests that the hydroxyl groups on the side chain may be essential for the uptake of occidiofungin into susceptible cells. This is supported by the fact that the dodecylamaine analog was capable of binding to actin in a similar manner as native occidiofungin. Given that the inhibitory activity of the dihydrosphingosine analog can be partially restored, the introduction of the hydroxyl groups near the base of the lipid moiety may aid in cellular entry and enable the analog to reach the actin target.

Accordingly, some embodiments of the invention provide modifying an occidiofungin analog disclosed herein to render it suitable for entry into the cell. Such modification can be attachment, for example, via a covalent bond, to a moiety that facilitates entry of the occidiofungin analog into a cell. Such modification can also be inclusion of the occidiofungin analogs disclosed herein into vesicles or capsules that facilitate uptake of the occidiofungin analog into a cell. The vesicles or capsules can be lipid vesicles or 1-Palmitoyl-2-oleoylphosphatidylcholine (POPC) vesicles.

Intravenous administration of occidiofungin triggered a mild inflammation or allergic response. Xylose is only reported to be present in plants and some invertebrates and is not known to be present in mammals. β-(1,2)-xylose is involved in a common cross-reactive antigenic determinant (CCD), and is shared by a variety of glycoproteins recognized by IgE antibodies of patients with food or respiratory allergies. Both IgE and IgG2 antibodies responded to CCDs and that CCDs affected both Th1- and Th2-type responses. β-(1,2)-xylose modifications of N-glycans modify specific IgE-binding in individuals allergic to Lyc e 2, a glycosylated allergen of tomato. The xylose free analogs of occidiofungin disclosed herein provide therapeutically superior analogs of occidiofungin.

The dihydrosphingosine analog exhibits low binding constant and saturation stoichiometry. The high saturation of occidiofungin to actin (25:1) can be attributed to the self-assembly mechanism of native occidiofungin monomers following its binding to F-actin. This is not uncommon activity for lipopeptides and the formation of self-assembled complexes was observed with several lipopeptide antibiotics. The polarity of dihydrosphingosine analog is much less than the native compound (eluted at 33% versus 47% water on HPLC; FIGS. 5-6), which might contribute to the loss of the self-assembly mechanism, in the sense that amphiphilicity leads to self-assembly at high concentrations for peptide amphiphiles. However, the relationship between self-assembly and bioactivity is complicated and remains unclear. Reduced antifungal activity of the dihydrosphingosine analog may be attributed to the reduced polarity and self-assembly property. The dihydrosphingosine analog had a Kd value of 25 nM and had a stoichiometry closer to a 1:1 (ligand:actin) binding. The dihydrosphingosine analog may have a higher affinity for actin. The lower Kd value likely represents the microscopic dissociation constant (which captures the affinity of one occidiofungin binding to actin) versus the macroscopic Kd value captured by the native compound (24:1 ligand:actin).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

1. Lu, S.-E., et al., *Occidiofungin, a Unique Antifungal Glycopeptide Produced by a Strain of Burkholderia contaminans*. Biochemistry, 2009. 48(35): p. 8312-8321.
2. Altmann, F., *The role of protein glycosylation in allergy*. International Archives Of Allergy And Immunology, 2007. 142(2): p. 99-115.
3. Hino, S., et al., *IgG2 dominancy and carbohydrate recognition specificity of C3H/He mouse antibodies directed to cross-reactive carbohydrate determinants (CCDs) bearing beta-(1,2)-xylose and alpha-(1,3)-fucose*. Immunology Letters, 2010. 133(1): p. 28-34.
4. Kaulffirst-Soboll, H., et al., *Reduction of cross-reactive carbohydrate determinants in plant foodstuff: elucidation of clinical relevance and implications for allergy diagnosis*. Plos One, 2011. 6(3): p. e17800-e17800.
5. Paulus, K. E., et al., *Silencing β1,2-xylosyltransferase in Transgenic Tomato Fruits Reveals xylose as Constitutive Component of Ige-Binding Epitopes*. Frontiers In Plant Science, 2011. 2: p. 42-42.
6. Steven Lai Hing, A. R., Jerome Escano, Jim Cooley, Frank Austin, Shi-En Lu, Stephen Pruett, Leif Smith, *Toxicological Evaluation of Occidiofungin against Mice and Human Cancer Cell Lines*. Scientific Research, 2014. 5(11).
7. Tan, W., et al., *Nonclinical toxicological evaluation of occidiofungin, a unique glycolipopeptide antifungal*. Int J Toxicol, 2012. 31(4): p. 326-36.
8. Emrick, D., et al., *The antifungal occidiofungin triggers an apoptotic mechanism of cell death in yeast*. J Nat Prod, 2013. 76(5): p. 829-38.
9. Control, C. f. D., *Candida auris Clinical Update—September 2017*. 2017.
10. Berkow, E. L. and S. R. Lockhart, *Fluconazole resistance in Candida species: a current perspective*. Infect Drug Resist, 2017. 10: p. 237-45.
11. Whaley, S. G., et al., *Azole Antifungal Resistance in Candida albicans and Emerging Non-albicans Candida Species*. Front Microbiol, 2016. 7:2173.
12. Perlin, D. S., *Echinocandin Resistance in Candida*. Clinical Infectious Diseases, 2015. 61(suppl 6): p. S612-S617.
13. Matheson, A. and D. Mazza, *Recurrent vulvovaginal candidiasis: A review of guideline recommendations*. Aust N Z J Obstet Gynaecol, 2017. 57(2): p. 139-145.
14. Sheary, B. and L. Dayan, *Recurrent vulvovaginal candidiasis*. Aust Fam Physician, 2005. 34(3): p. 147-50.
15. Sobel, J. D., *Pathogenesis and treatment of recurrent vulvovaginal candidiasis*. Clin Infect Dis, 1992. 14 Suppl 1: p. S148-53.
16. Ramsay, S., et al., *Practical management of recurrent vulvovaginal candidiasis*. Trends in Urology, Gynaecology & Sexual Health, 2009. 14(6): p. 18-22.
17. Goncalves, B., et al., *Vulvovaginal candidiasis: Epidemiology, microbiology and risk factors*. Crit Rev Microbiol, 2016. 42(6): p. 905-27.
18. Watson, C. and H. Calabretto, *Comprehensive review of conventional and non-conventional methods of management of recurrent vulvovaginal candidiasis*. Aust N Z J Obstet Gynaecol, 2007. 47(4): p. 262-72.
19. Charlier, C., et al., *Fluconazole for the management of invasive candidiasis: where do we stand after 15 years?* J Antimicrob Chemother, 2006. 57(3): p. 384-410.
20. Hibberd, P. L. and R. H. Rubin, *Clinical aspects of fungal infection in organ transplant recipients*. Clin Infect Dis, 1994. 19 Suppl 1: p. S33-40.
21. Schaenman, J. M., et al., *Trends in invasive disease due to Candida species following heart and lung transplantation*. Transpl Infect Dis, 2009. 11(2): p. 112-21.
22. Dauber, J. H., I. L. Paradis, and J. S. Dummer, *Infectious complications in pulmonary allograft recipients*. Clin Chest Med, 1990. 11(2): p. 291-308.
23. Dummer, J. S., et al., *Infections in heart-lung transplant recipients*. Transplantation, 1986. 41(6): p. 725-9.

24. Kanj, S. S., et al., *Fungal infections in lung and heart-lung transplant recipients. Report of 9 cases and review of the literature.* Medicine (Baltimore), 1996. 75(3): p. 142-56.
25. Kubak, B. M., *Fungal infection in lung transplantation.* Transpl Infect Dis, 2002. 4 Suppl 3: p. 24-31.
26. Montoya, J. G., et al., *Infectious complications among 620 consecutive heart transplant patients at Stanford University Medical Center.* Clin Infect Dis, 2001. 33(5): p. 629-40.
27. Cuenca-Estrella, M., et al., *In vitro susceptibilities of bloodstream isolates of Candida species to six antifungal agents: results from a population-based active surveillance programme*, Barcelona, Spain, 2002-2003. J Antimicrob Chemother, 2005. 55(2): p. 194-9.
28. Edmond, M. B., et al., *Nosocomial bloodstream infections in United States hospitals: a three-year analysis.* Clin Infect Dis, 1999. 29(2): p. 239-44.
29. Jeffery-Smith, A., et al., *Candida auris: a Review of the Literature.* Clin Microbiol Rev, 2018. 31: e00029-17.
30. McCarthy, M., *Hospital transmitted <em> Candida auris</em> infections confirmed in the US.* BMJ, 2016. 355.
31. Messer, S. A., R. N. Jones, and T. R. Fritsche, International surveillance of Candida spp. and Aspergillus spp.: Report from the SENTRY Antimicrobial Surveillance Program (2003). Journal of Clinical Microbiology, 2006. 44(5): p. 1782-1787.
32. Sheehan, D. J., C. A. Hitchcock, and C. M. Sibley, *Current and emerging azole antifungal agents.* Clin Microbiol Rev, 1999. 12(1): p. 40-79.
33. Sugar, A. M., *The polyene macrolide antifungal drugs.* Antimicrobial Agents. 1986.
34. Graybill, J. R., *The echinocandins, first novel class of antifungals in two decades: will they live up to their promise?* Int J Clin Pract, 2001. 55(9): p. 633-8.
35. Hector, R. F., *Compounds active against cell walls of medically important fungi.* Clin Microbiol Rev, 1993. 6(1): p. 1-21.
36. Joseph-Horne, T. and D. W. Hollomon, *Molecular mechanisms of azole resistance in fungi.* FEMS Microbiol Lett, 1997. 149(2): p. 141-9.
37. Rosana, Y, A. Yasmon, and D. C. Lestari, *Overexpression and mutation as a genetic mechanism of fluconazole resistance in Candida albicans isolated from human immunodeficiency virus patients in Indonesia.* J Med Microbiol, 2015. 64(9): p. 1046-52.
38. Sanguinetti, M., et al., *Mechanisms of azole resistance in clinical isolates of Candida glabrata collected during a hospital survey of antifungal resistance.* Antimicrob Agents Chemother, 2005. 49(2): p. 668-79.
39. Kurtz, M. B. and C. M. Douglas, *Lipopeptide inhibitors of fungal glucan synthase.* J Med Vet Mycol, 1997. 35(2): p. 79-86.
40. Ghannoum, M. A. and L. B. Rice, *Antifungal Agents: Mode of Action, Mechanisms of Resistance, and Correlation of These Mechanisms with Bacterial Resistance.* Clinical Microbiology Reviews, 1999. 12(4): p. 501-517.
41. Ashley, E. S. D., et al., *Pharmacology of Systemic Antifungal Agents.* Clinical Infectious Diseases, 2006. 43(Supplement 1): p. S28-S39.
42. Lewis, R. E., *Current Concepts in Antifungal Pharmacology.* Mayo Clin Proc, 2011. 86(8): p. 805-17.
43. Denning, D. W. and M. J. Bromley, *Infectious Disease. How to bolster the antifungal pipeline.* Science, 2015. 347(6229): p. 1414-6.
44. Matheson, A. and D. Mazza, *Recurrent vulvovaginal candidiasis: A review of guideline recommendations.* The Australian & New Zealand Journal Of Obstetrics & Gynaecology, 2017. 57(2): p. 139-145.
45. Sheary, B. and L. Dayan, *Recurrent vulvovaginal candidiasis.* Australian Family Physician, 2005. 34(3): p. 147-150.
46. Sobel, J. D., *Pathogenesis and treatment of recurrent vulvovaginal candidiasis.* Clinical Infectious Diseases: An Official Publication Of The Infectious Diseases Society Of America, 1992. 14 Suppl 1: p. S148-S153.
47. Foxman, B., et al., *Candida Vaginitis, Self Reported Incidence and Associated Costs.* Sexually Transmitted Diseases, 27(4): p. 230-235.
48. L. E. K., *Consulting primary research on vulvovaginal candidiasis conducted in 2,400 US women.* 2011.
49. Gu, G., et al., *Genetic and biochemical map for the biosynthesis of occidiofungin, an antifungal produced by Burkholderia contaminans strain MS14.* Applied And Environmental Microbiology, 2011. 77(17): p. 6189-6198.
50. Gu, G. Y, et al., *Biosynthesis of an antifungal oligopeptide in Burkholderia contaminans strain MS14.* Biochemical And Biophysical Research Communications, 2009. 380(2): p. 328-332.
51. Ellis, D., et al., *Occidiofungin's Chemical Stability and In vitro Potency Against Candida species.* Antimicrob Agents Chemother, 2012. 56(2): p. 765-769.
52. Emrick, D., et al., *The antifungal occidiofungin triggers an apoptotic mechanism of cell death in yeast.* Journal Of Natural Products, 2013. 76(5): p. 829-838.
53. Wei, T., et al., *Pre-clinical Toxicological Evaluation of Occidiofungin, a Unique Glyco-lipopeptide Antifungal.* International Journal of Toxicology, 2012. 31(4): p. 326-336.
54. Yano, J. and J. P. L. Fidel, *Protocols for Vaginal Inoculation and Sample Collection in the Experimental Mouse Model of Candida vaginitis.* Journal of Visualized Experiments: JoVE, 2011(58): p. 3382.
55. González, G. M., et al., *Therapeutic efficacy of voriconazole against a fluconazole-resistant Candida albicans isolate in a vaginal model.* Journal of Antimicrobial Chemotherapy, 2009. 64(3): p. 571-573.
56. Centers for Disease Control and Prevention. 2017. *Candida auris clinical update—September 2017.* Centers for Disease Control and Prevention, Atlanta, GA
57. Perlin D S. 2007. Resistance to echinocandin-class antifungal drugs, Drug Resistance Updates, 10: 121-130.
58. US Food and Drug Administration, 2013. FDA Drug Safety Communication: FDA limits usage of Nizoral (ketoconazole) oral tablets due to potentially fatal liver injury and risk of drug interactions and adrenal gland problems. Drugs. October, 16.
59. European Medicines Agency, 2013. European Medicines Agency recommends suspension of marketing authorisations for oral ketoconazole. Eur Med Agency, pp. 1-3.
60. Ravichandran A, Geng M, Hull K G, et al. 2018. A novel actin binding drug with in vivo efficacy. Antimicrobial agents and chemotherapy, AAC01585-18.
61. Tan, W., Cooley, J., Austin, F., Lu, S. E., Pruett, S. B., Smith, L. 2012. Nonclinical toxicological evaluation of occidiofungin, a unique glycolipopeptide antifungal. International journal of toxicology, 31: 326-336.
62. Zhang J Y, Liu J H, Liu F D, Xia V H, Wang J, Liu X, Zhang Z Q, Zhu N, Yan Y, Ying Y, Huang X T. 2014.

Vulvovaginal candidiasis: species distribution, fluconazole resistance and drug efflux pump gene overexpression. Mycoses 57:584-591.
63. Fling, S. L., Ravichandran, A., Escano, J., Cooley, J., Austin, F., Lu, S. E., Smith, L. 2014. Toxicological evaluation of occidiofungin against mice and human cancer cell lines. Pharmacology & Pharmacy, 5: 1085.
64. Smith J A. 1994. Neutrophils, host defense, and inflammation: a double-edged sword. Journal of leukocyte biology, 56: 672-686.
65. Fötisch K, Vieths S. 2001. N- and O-linked oligosaccharides of allergenic glycoproteins. Glycoconjugate Journal, 18: 373-390,
66. Chen, K. C., Ravichandran, A., Guerrero, A., Deng, P., Baird, S. M., Smith, L., Lu, S. E. 2013. The *Burkholderia contaminans* MS14 ocfC gene encodes a xylosyltransferase for production of the antifungal occidiofungin. Applied and environmental microbiology, 79: 2899-2905.
67. Malaprade, M. L., 1934. Bull. Soc. Chim, Franc., 5, 833.
67. Price, C. C., Kroll, H. 1938. The kinetics of the periodate oxidation of 1, 2-glycols. Journal of the American Chemical Society, 60: 2726-2729.
68. Abdel-Magid, A. F., Carson, K. G., Harris, B. D., Maryanoff, C. A., Shah, R. D. 1996. Reductive amination of aldehydes and ketones with sodium triacetoxyborohydride. studies on direct and indirect reductive amination procedures1. The Journal of organic chemistry, 61: 3849-3862,
69. De La Cruz, E. M., Pollard, T. 1996. Kinetics and thermodynamics of phalloidin binding to actin filaments from three divergent species. Biochemistry, 35: 14054-14061.
70. Coluccio, L. M., Tilney, L. G. 1984. Phalloidin enhances actin assembly by preventing monomer dissociation. The Journal of cell biology, 99: 529-535.
71. Cooper, J. A. 1987. Effects of cytochalasin and phalloidin on actin. The Journal of cell biology, 105: 1473-1478.
72. Faergeman, N. J., DiRusso, C. C., Elberger, A., Knudsen, J., Black, P, N. 1997. Disruption of the *Saccharomyces cerevisiae* homologue to the murine fatty acid transport protein impairs uptake and growth on long-chain fatty acids. Journal of Biological Chemistry, 272: 8531-8538.
73. Tehlivets O, Scheuringer K, Kohlwein S D. 2007. Fatty acid synthesis and elongation in yeast. Biochimica et Biophysica Acta (BBA)-Molecular and Cell Biology of Lipids, 1771: 255-270.
74. Un, K., Sakai-Kato, K. Oshima, Y., Kawanishi, T., Okuda, H. 2012. Intracellular trafficking mechanism, from intracellular uptake to extracellular efflux, for phospholipid/cholesterol liposomes. Biomaterials, 33: 8131-8141.
75. Mari A. 2002. IgE to cross-reactive carbohydrate determinants: analysis of the distribution and appraisal of the in vivo and in vitro reactivity. International archives of allergy and immunology, 129: 286-295.
76. Hamley I W. 2015. Lipopeptides: from self-assembly to bioactivity. Chemical Communications, 51: 8574-8583.
77. Hamley, I. W. 2011. Self-assembly of amphiphilic peptides. Soft Matter, 7: 78.4122-4138. Bubb M R, Senderowicz A M, Sausville E A, Duncan K L, Korn E D. 1994. Jasplakinolide, a cytotoxic natural product, induces actin polymerization and competitively inhibits the binding of phalloidin to F-actin, J Biol Chem 269:14869-14871.
79. Chung S-C, Lee S-H, Jang K H, Park W, Jeon J-e, Oh H, Shin J, Oh K B. 2011. Actin depolymerizing effect of trisoxazole-containing macrolides. Bioorg Med Chem Lett 21:3198-3201.
80. Li. Z. Geng M, Yang H. 2015. Algicidal activity of *Bacillus* sp. Lzh-5 and its algicidal compounds against *Microcystis aeruginosa*. Applied microbiology and biotechnology, 99: 981-990.
81. Wüthrich, K., 1986. NMR with Proteins and Nucleic Acids. Europhysics News, 17:11-13.
82. Braunschweiler, L., Ernst, R. R. 1983. Coherence transfer by isotropic mixing:
application to proton correlation spectroscopy. Journal of Magnetic Resonance (1969).53:521-528,
83. Kumar, A., Ernst, R. R. Wüthrich, K. 1980. A two-dimensional nuclear Overhauser enhancement (2D NOE) experiment for the elucidation of complete proton-proton cross-relaxation networks in biological macromolecules. Biochemical and biophysical research communications, 95:1-6.
84. Bodenhausen, G., Ruben, D. J. 1980. Natural abundance nitrogen-15 NMR by enhanced heteronuclear spectroscopy. Chemical Physics Letters, 69:185-189.
85. Johnson, B. A., Blevins, R. A. 1994. NMR View: A computer program for the visualization and analysis of NMR data. Journal of biomolecular NMR, 4:603-614.

We claim:

1. A compound or salt thereof selected from the group consisting of:

a) a compound of Formula II or a salt thereof:

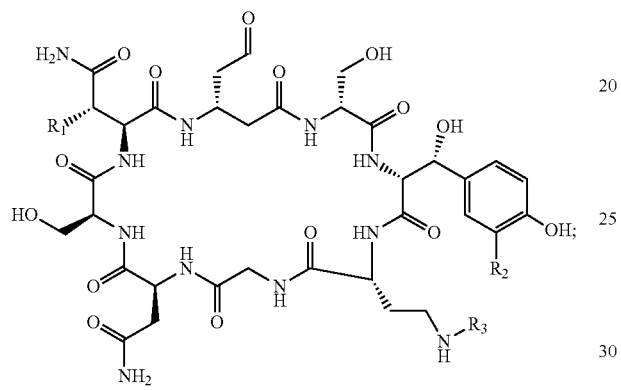

Occidiofungin A: $R_1$ = H, $R_2$ = H, $R_3$ = H or $(CO)CH_2CH_2CH_2C{\equiv}CH$,
Occidiofungin B: $R_1$ = OH, $R_2$ = H, $R_3$ = H or $(CO)CH_2CH_2CH_2C{\equiv}CH$,
Occidiofungin C: $R_1$ = H, $R_2$ = Cl, $R_3$ = H or $(CO)CH_2CH_2CH_2C{\equiv}CH$,
or
Occidiofungin D: $R_1$ = OH, $R_2$ = Cl, $R_3$ = H or $(CO)CH_2CH_2CH_2C{\equiv}CH$;

b) a compound of Formula III or a salt thereof:

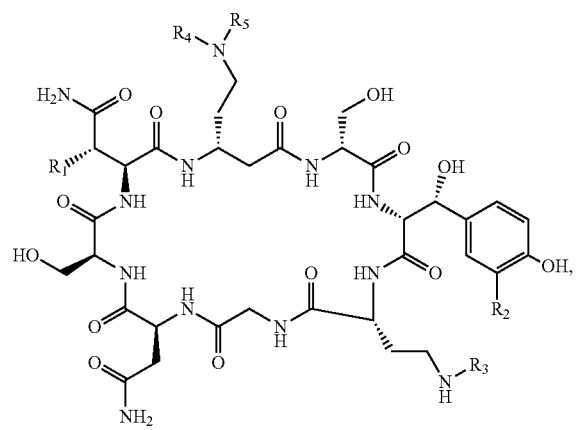

Occidiofungin A: $R_1$ = H, $R_2$ = H, $R_3$ = H or $(CO)CH_2CH_2CH_2C{\equiv}CH$,
Occidiofungin B: $R_1$ = OH, $R_2$ = H, $R_3$ = H or $(CO)CH_2CH_2CH_2C{\equiv}CH$,
Occidiofungin C: $R_1$ = H, $R_2$ = Cl, $R_3$ = H or $(CO)CH_2CH_2CH_2C{\equiv}CH$,
or
Occidiofungin D: $R_1$ = OH, $R_2$ = Cl, $R_3$ = H or $(CO)CH_2CH_2CH_2C{\equiv}CH$, and wherein $R_4$ or $R_5$ of Formula III is independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone, dihydrosphingosine, or a halogen;

c) a compound of Formula IV or a salt thereof:

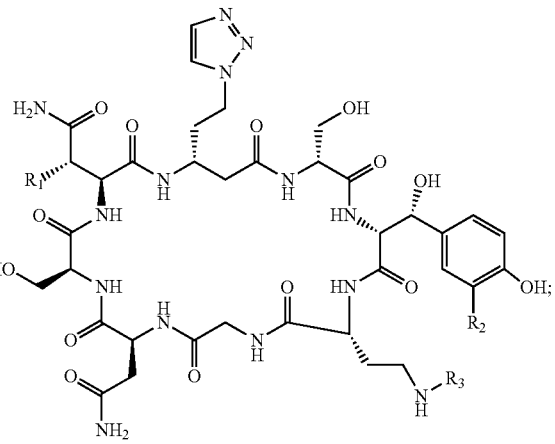

Occidiofungin A: $R_1$ = H, $R_2$ = H, $R_3$ = H or $(CO)CH_2CH_2CH_2C{\equiv}CH$,
Occidiofungin B: $R_1$ = OH, $R_2$ = H, $R_3$ = H or $(CO)CH_2CH_2CH_2C{\equiv}CH$,
Occidiofungin C: $R_1$ = H, $R_2$ = Cl, $R_3$ = H or $(CO)CH_2CH_2CH_2C{\equiv}CH$,
or
Occidiofungin D: $R_1$ = OH, $R_2$ = Cl, $R_3$ = H or $(CO)CH_2CH_2CH_2C{\equiv}CH$;

d) a compound of Formula V or a salt thereof:

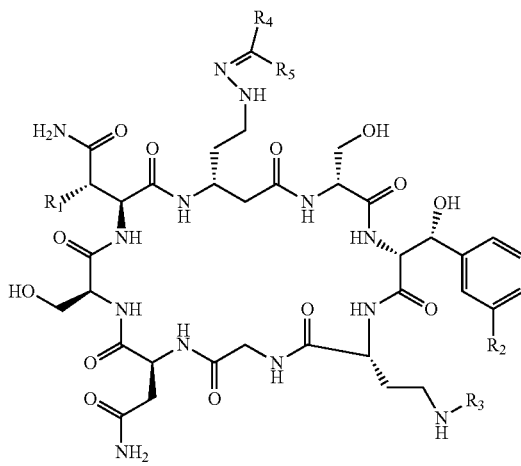

Occidiofungin A: $R_1$ = H, $R_2$ = H, $R_3$ = H or (CO)CH$_2$CH$_2$CH$_2$C≡CH,
Occidiofungin B: $R_1$ = OH, $R_2$ = H, $R_3$ = H or (CO)CH$_2$CH$_2$CH$_2$C≡CH,
Occidiofungin C: $R_1$ = H, $R_2$ = Cl, $R_3$ = H or (CO)CH$_2$CH$_2$CH$_2$C≡CH, or
Occidiofungin D: $R_1$ = OH, $R_2$ = Cl, $R_3$ = H or (CO)CH$_2$CH$_2$CH$_2$C≡CH, and $R_4$ or $R_5$ are independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen.

2. The compound or salt according to claim 1, wherein said compound or salt thereof is a compound of Formula II:

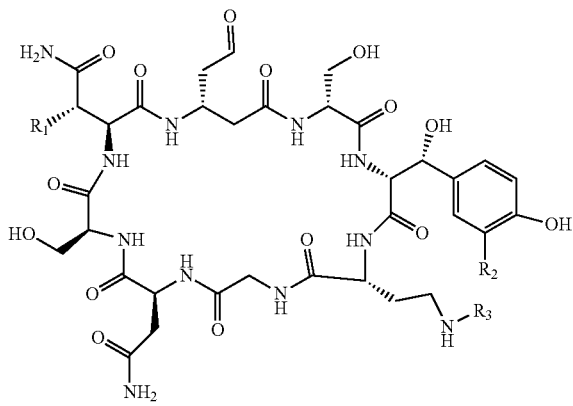

Occidiofungin A: $R_1$ = H, $R_2$ = H, $R_3$ = H or (CO)CH$_2$CH$_2$CH$_2$C≡CH,
Occidiofungin B: $R_1$ = OH, $R_2$ = H, $R_3$ = H or (CO)CH$_2$CH$_2$CH$_2$C≡CH,
Occidiofungin C: $R_1$ = H, $R_2$ = Cl, $R_3$ = H or (CO)CH$_2$CH$_2$CH$_2$C≡CH, or
Occidiofungin D: $R_1$ = OH, $R_2$ = Cl, $R_3$ = H or (CO)CH$_2$CH$_2$CH$_2$C≡CH.

3. The compound or salt according to claim 2, wherein said compound or salt is occidiofungin A, occidiofungin B, occidiofungin C, or occidiofungin D.

4. The compound or salt according to claim 1, wherein said compound or salt thereof is a compound of Formula III:

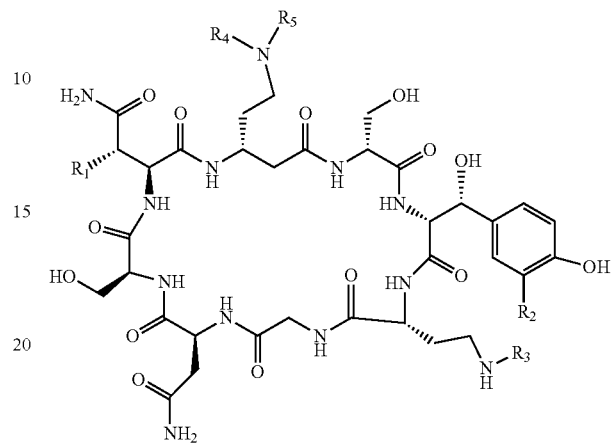

Occidiofungin A: $R_1$ = H, $R_2$ = H, $R_3$ = H or (CO)CH$_2$CH$_2$CH$_2$C≡CH,
Occidiofungin B: $R_1$ = OH, $R_2$ = H, $R_3$ = H or (CO)CH$_2$CH$_2$CH$_2$C≡CH,
Occidiofungin C: $R_1$ = H, $R_2$ = Cl, $R_3$ = H or (CO)CH$_2$CH$_2$CH$_2$C≡CH, or
Occidiofungin D: $R_1$ = OH, $R_2$ = Cl, $R_3$ = H or (CO)CH$_2$CH$_2$CH$_2$C≡CH, and wherein $R_4$ or $R_5$ of Formula III is independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone, dihydrosphingosine, or a halogen.

5. The compound or salt according to claim 4, wherein $R_4$ or $R_5$ are independently H, OH, unsubstituted alkane, unsubstituted alkene, unsubstituted alkyne, unsubstituted aryl, unsubstituted heterocycle, unsubstituted heteroaryl, unsubstituted heterocycle, unsubstituted ether, unsubstituted thioether, unsubstituted ketone, dihydrosphingosine, or a halogen.

6. The compound or salt according to claim 4, wherein said compound or salt is occidiofungin A, occidiofungin B, occidiofungin C, or occidiofungin D and $R_4$ or $R_5$ are independently H, OH, unsubstituted alkane, unsubstituted alkene, unsubstituted alkyne, unsubstituted aryl, unsubstituted heterocycle, unsubstituted heteroaryl, unsubstituted heterocycle, ether, unsubstituted thioether, unsubstituted ketone, dihydrosphingosine, or a halogen.

7. The compound or salt according to claim 4, wherein said compound or salt is occidiofungin A, occidiofungin B, occidiofungin C, or occidiofungin D and $R_4$ or $R_5$ are independently H, OH, a substituted or unsubstituted alkane, substituted or unsubstituted alkene, substituted or unsubstituted alkyne, substituted or unsubstituted aryl, substituted or unsubstituted heteroaryl, substituted or unsubstituted heterocycle, substituted or unsubstituted ether, substituted or unsubstituted thioether, substituted or unsubstituted ketone, dihydrosphingosine, or a halogen.

8. The compound or salt according to claim 1, wherein said compound or salt thereof is a compound of Formula IV:

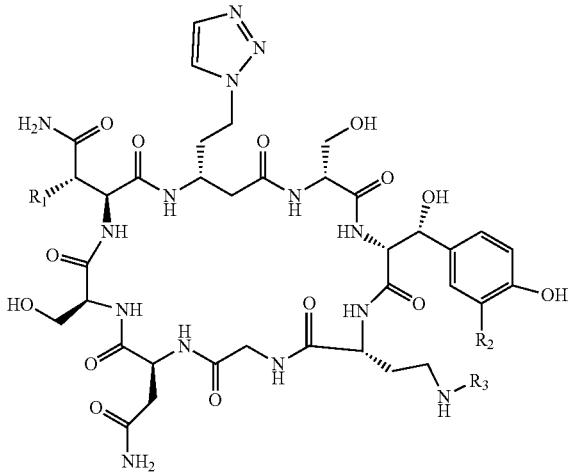

Occidiofungin A: R₁ = H, R₂ = H, R₃ = H or (CO)CH₂CH₂CH₂C≡CH,
Occidiofungin B: R₁ = OH, R₂ = H, R₃ = H or (CO)CH₂CH₂CH₂C≡CH,
Occidiofungin C: R₁ = H, R₂ = Cl, R₃ = H or (CO)CH₂CH₂CH₂C≡CH, or
Occidiofungin D: R₁ = OH, R₂ = Cl, R₃ = H or (CO)CH₂CH₂CH₂C≡CH.

9. The compound or salt according to claim 8, wherein said compound or salt is occidiofungin A, occidiofungin B, occidiofungin C, or occidiofungin D.

10. The compound or salt according to claim 1, wherein said compound or salt thereof is a compound of Formula V:

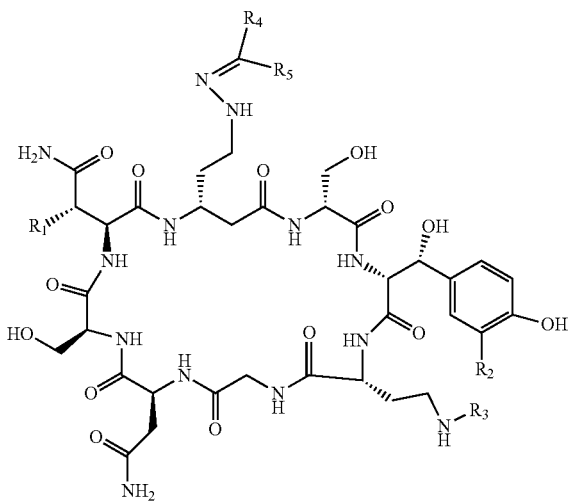

Occidiofungin A: R₁ = H, R₂ = H, R₃ = H or (CO)CH₂CH₂CH₂C≡CH,
Occidiofungin B: R₁ = OH, R₂ = H, R₃ = H or (CO)CH₂CH₂CH₂C≡CH,
Occidiofungin C: R₁ = H, R₂ = Cl, R₃ = H or (CO)CH₂CH₂CH₂C≡CH, or
Occidiofungin D: R₁ = OH, R₂ = Cl, R₃ = H or (CO)CH₂CH₂CH₂C≡CH, and $R_4$ or $R_5$ are independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone or a halogen.

11. The compound or salt according to claim 10, wherein $R_4$ or $R_5$ are independently H, OH, unsubstituted alkane, unsubstituted alkene, unsubstituted alkyne, unsubstituted aryl, unsubstituted heterocycle, unsubstituted heteroaryl, unsubstituted heterocycle, unsubstituted ether, unsubstituted thioether, unsubstituted ketone or a halogen.

12. The compound or salt according to claim 10, wherein said compound or salt is occidiofungin A, occidiofungin B, occidiofungin C, or occidiofungin D and $R_4$ or $R_5$ are independently H, OH, a substituted or unsubstituted alkane, substituted or unsubstituted alkene, substituted or unsubstituted alkyne, substituted or unsubstituted aryl, substituted or unsubstituted heterocycle, substituted or unsubstituted heteroaryl, substituted or unsubstituted heterocycle, substituted or unsubstituted ether, substituted or unsubstituted thioether, substituted or unsubstituted ketone, dihydrosphingosine, or a halogen.

13. A pharmaceutical composition comprising a compound or salt according to claim 1 and a pharmaceutically acceptable vehicle.

14. A pharmaceutical composition comprising a compound or salt according to claim 4 and a pharmaceutically acceptable vehicle.

15. A pharmaceutical composition comprising a compound or salt according to claim 6 and a pharmaceutically acceptable vehicle.

16. A method of treating a fungal infection, comprising administering to a subject in need thereof an effective amount of a compound or salt according to claim 1 or a pharmaceutical composition thereof.

17. The method of claim 16, comprising administering the compound, salt, or the pharmaceutical composition intravaginally, intramuscularly, subcutaneously, intrathecally, intravenously or intraperitoneally.

18. The method of claim 16, wherein the fungal infection is caused by a *Candida* spp., *Trichophyton* spp., *Rhizopus* spp., *Mucor* spp., *Fusarium* spp., *Aspergillus* spp. or *Cryptococcus* spp.

19. The method of claim 18, wherein the *Candida* spp. is *C. albicans, C. glabrata, C. krusei, C. krusei, C. parapsilosis* or *C. tropicalis.*

* * * * *

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (2)..(2)
<223> OTHER INFORMATION: Xaa = 3 amino-5,6-dihydroxy-7-O-xylose-
     octadecanoic acid
<220> FEATURE:
<221> NAME/KEY: MISC_FEATURE
```

```
<222> LOCATION: (4)..(4)
<223> OTHER INFORMATION: Xaa = beta-hydroxy tyrosine

<400> SEQUENCE: 1

Asn Xaa Ser Xaa Gly Asn Ser
1               5
```